(12) United States Patent
Dmochowski et al.

(10) Patent No.: US 8,222,022 B2
(45) Date of Patent: Jul. 17, 2012

(54) TRI-FUNCTIONALIZED CRYPTOPHANE BIOSENSORS

(75) Inventors: Ivan Dmochowski, Philadelphia, PA (US); Aru P. Hill, Oakland, CA (US); Qian Wei, Delran, NJ (US); Jennifer M. Chambers, Ivanhoe (AU)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 331 days.

(21) Appl. No.: 12/498,858

(22) Filed: Jul. 7, 2009

(65) Prior Publication Data
US 2010/0105099 A1    Apr. 29, 2010

Related U.S. Application Data

(60) Provisional application No. 61/129,576, filed on Jul. 7, 2008.

(51) Int. Cl.
*C12M 3/00*    (2006.01)
(52) U.S. Cl. ...................................... 435/287.1; 435/7.1
(58) Field of Classification Search .................. 435/9.34, 435/7.1
See application file for complete search history.

(56) References Cited

U.S. PATENT DOCUMENTS 7,385,395 B2 * 6/2008 Pines et al. .................... 324/301
2011/0104075 A1 * 5/2011 Dmochowski et al. ...... 424/9.34

OTHER PUBLICATIONS

Huber J. et al. NMR Study of Optically Active Monosubstituted Cryptophanes and Their Interaction with Xenon. J Physical Chem 108:9608-9615, 2004.*
Chambers J. et al. Cryptophane Xenon 129 NMR Biosensors Targeting Human Carbonic Anhydrase. JACS 13(2)563-569, Jan. 21, 2009.*
Spence M. et al. Development of a Functionalized Biosensor. JACS 126:15287-15294, 2004.*

* cited by examiner

*Primary Examiner* — Ralph Gitomer
(74) *Attorney, Agent, or Firm* — Mark S. Cohen; Pearl Cohen Zedek Latzer, LLP

(57) ABSTRACT

This invention relates to biosensors with improved solubility and affinity to a noble element. Specifically, the invention relates to methods and systems for the detection of target entities using the signal observed in a noble element complexed to the biosensor.

9 Claims, 19 Drawing Sheets a

1-M₀M₀   1-P₀P₀ b

TRI-FUNCTIONALIZED CRYPTOPHANE BIOSENSORS

CROSS REFERENCE TO RELATED APPLICATIONS

This application claims priority to U.S. provisional patent application 61/129,576, filed Jul. 7, 2008, which is incorporated herein by reference in its entirety.

GOVERNMENT INTEREST

The invention was supported, in part, by the National Institute of Health (Grant Numbers 1R21CA110104, 1R33CA110104, and 1S10RR021113-01) and the Department of Defense (Grant No. W81XWH-04-1-0657). The United States government may have certain rights in the invention.

FIELD OF THE INVENTION

The invention relates to biosensors with improved solubility and affinity to a noble element. Specifically, the invention relates to methods and systems for the detection of target entities using the signal observed in a noble element complexed to the biosensor.

BACKGROUND OF THE INVENTION

Xenon-129 biosensors offer exciting potential for the simultaneous magnetic resonance imaging (MRI) of multiple frequency-resolved biomolecular targets. In addition to being a relatively abundant isotope of a non-toxic noble gas, the xenon-129 nucleus is spin-½ and can be laser-polarized to increase nuclear magnetic resonance (NMR) signals more than 10,000-fold. The polarizability of the xenon electron cloud imparts considerable environmental sensitivity to the chemical shift of the $^{129}$Xe nucleus, producing a nearly 300 ppm $^{129}$Xe NMR chemical shift window in common solvents. This sensitivity facilitates the simultaneous detection of monatomic $^{129}$Xe in different chemical environments. Biosensors exploiting this property have been generated by attaching a xenon-binding cryptophane-A moiety to protein-specific ligands such as biotin or protease-specific peptides. Cryptophane-based biosensors can be spectrally and spatially resolved in MR imaging and the cryptophane has been shown to be a competent xenon binder under near-physiological conditions.

Accordingly, there is a need in the art for improved xenon-binding host molecules in both organic and aqueous phase.

SUMMARY OF THE INVENTION

In one embodiment, the invention provides a biosensor comprising a hyperpolarized noble element complexed with a tri-functionalized cryptophane, wherein the tri-functionalized cryptophane is comprised of first and second cyclotriveratrylene (CTV) units. In some embodiments, the tri-functionalized cryptophane incorporates a dipole moment between the first and second cyclotriveratrylene (CTV) units.

In another embodiment, the invention provides a composition comprising a hyperpolarized noble element complexed with a tri-functionalized cryptophane, wherein the to tri-functionalized cryptophane is comprised of first and second cyclotriveratrylene (CTV) units.

In another embodiment, the invention provides a method of synthesizing a tri-functionalized cryptophane, comprising the steps of: in the presence of DMF, deprotonating cyclotriveratrylene (CTV), using cesium carbonate and reacting the deprotonated cyclotriveratrylene with 2-[3-allyloxy-4-(2-iodo-ethoxy)-benzyloxy]-tetrahydropyran yielding 2,7,12-tris[2-[4-(hydroxymethyl)-2-propargyloxyphenoxy]ethoxy]-3,8,13-trimethoxy-10,15-dihydro-2H-tribenzo[a,d,g]cyclononene; in the presence of an organic solvent, cyclizing the resulting 2,7,12-tris[2-[4-(hydroxymethyl)-2-propargyloxyphenoxy]ethoxy]-3,8,13-trimethoxy-10,15-dihydro-2H-tribenzo[a,d,g]cyclononene, obtaining triallyl-cryptophane; deprotecting the triallyl-cryptophane using a catalyst, thereby obtaining triphenol-cryptophane; alkylating the triphenol-cryptophane using a functionalizing molecule in the presence of cesium carbonate in DMF, thereby obtaining triester-cryptophane, whereby the triester is of the functionalizing molecule; and saponifying the triester-cryptophane in tetrahydrofuran using potassium hydroxide thereby obtaining triacid-functionalized, water-soluble cryptophane.

In another embodiment, the invention provides a method for synthesizing a tri-functionalized cryptophane, comprising the steps of: obtaining a functionalized cyclotriveratrylene (CTV) intermediate by a process that eliminates the need for allyl group protection or deprotection; reacting said intermediate with three equivalents of benzaldehyde; and cyclizing with scandium triflate, thereby obtaining said tri-functionalized cryptophane. In an exemplary embodiment, the intermediate is tri-(2-bromoethyl)cyclotriveratrylene (CTV) and the tri-functionalized cryptophane is tri-propargyl cryptophane.

In one embodiment, the invention provides a method of synthesizing a biosensor having increased affinity for a noble element, comprising the steps of: mediated by Cu(I), coupling a tri-functionalized cryptophane with an affinity tag; and complexing a hyperpolarized noble element with the tri-functionalized cryptophane coupled tag, wherein the tri-functionalized cryptophane includes first and second cyclotriveratrylene (CTV) units and wherein a dipole moment exists between said first and second cyclotriveratrylene (CTV).

In another embodiment, the invention provides a method of detecting the activity of a α-carbonic anhydrase (CA) isoenzyme in a biological sample of a subject, comprising the step of contacting the biological sample with a biosensor comprising a hyperpolarized noble element complexed to a tri-functionalized cryptophane coupled affinity tag, wherein the affinity tag is specific to said α-carbonic anhydrase isoenzyme; and analyzing the signal in said element, whereby a signal indicates activity of said α-carbonic anhydrase isoenzyme.

In one embodiment, the invention provides a method of diagnosing a disease associated with α-carbonic anhydrase isoenzyme expression in a subject, comprising the step of obtaining a biological sample from said subject; contacting the biological sample with a biosensor comprising a hyperpolarized noble element complexed to a tri-functionalized cryptophane coupled affinity tag, wherein the affinity tag is specific to said α-carbonic anhydrase isoenzyme; analyzing the signal in said element; and comparing the signal obtained from the sample with a signal obtained under the same conditions in a standard.

In another embodiment, the invention provides a method for screening for a candidate agent capable of modulating the activity of a protein in a biological sample, comprising the step of contacting a first portion of the biological sample with a biosensor comprising a hyperpolarized noble element complexed to a tri-functionalized cryptophane coupled affinity tag, wherein the affinity tag is specific for the protein sought to be modulated and analyzing the signal of said element; contacting a second portion with the candidate agent screened; contacting the second portion with the same biosensor; and comparing the detected signal in the second portion, whereby a difference in the signal between the first and second portions indicates said agent being capable of modulating the activity of the protein.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1:
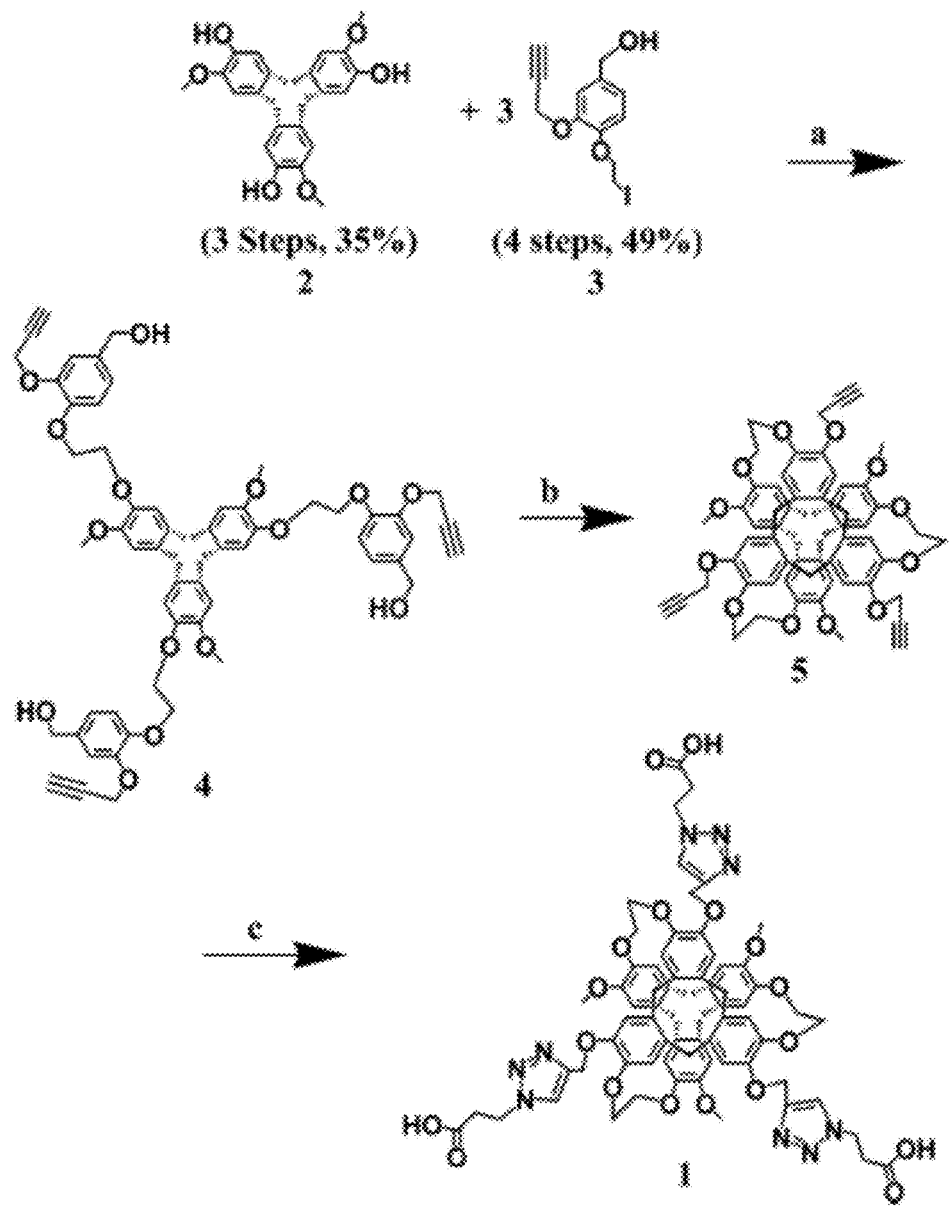
FIG. 1 shows a ten-step synthesis schematic of cryptophane.

The invention relates to biosensors with improved solubility and affinity to a noble element. Specifically, the invention relates to methods and systems for the detection of target entities using the signal observed in a noble element complexed to the biosensor.

In one embodiment, provided herein is a biosensor comprising a hyperpolarized noble element complexed with a tri-functionalized cryptophane, wherein the tri-functionalized cryptophane is comprised of first and second cyclotriveratrylene (CTV) units. In some embodiments, the tri-functionalized cryptophane incorporates a dipole moment between the first and second cyclotriveratrylene (CTV) units.

In another embodiment, provided herein is a composition comprising a hyperpolarized noble element complexed with a tri-functionalized cryptophane, wherein the tri-functionalized cryptophane is comprised of first and second cyclotriveratrylene (CTV) units.

In another embodiment, provided herein is a method of synthesizing a tri-functionalized cryptophane, comprising the steps of: in the presence of DMF, deprotonating cyclotriveratrylene (CTV), using cesium carbonate and reacting the deprotonated cyclotriveratrylene with 2-[3-allyloxy-4-(2-iodo-ethoxy)-benzyloxy]-tetrahydropyran yielding 2,7,12-tris[2-[4-(hydroxymethyl)-2-propargyloxyphenoxy]ethoxy]-3,8,13-trimethoxy-10,15-dihydro-2H-tribenzo[a,d,g]cyclononene; in the presence of an organic solvent, cyclizing the resulting 2,7,12-tris[2-[4-(hydroxymethyl)-2-propargyloxyphenoxy]ethoxy]-3,8,13-trimethoxy-10,15-dihydro-2H-tribenzo[a,d,g]cyclononene, obtaining triallyl-cryptophane; deprotecting the triallyl-cryptophane using a catalyst, thereby obtaining triphenol-cryptophane; alkylating the triphenol-cryptophane using a functionalizing molecule in the presence of cesium carbonate in DMF, thereby obtaining triester-cryptophane, whereby the triester is of the functionalizing molecule; and saponifying the triester-cryptophane in tetrahydrofuran using potassium hydroxide thereby obtaining triacid-functionalized, water-soluble cryptophane.

In another embodiment, provided herein is a method for synthesizing a tri-functionalized cryptophane, comprising the steps of: obtaining a functionalized cyclotriveratrylene (CTV) intermediate by a process that eliminates the need for allyl group protection or deprotection; reacting said intermediate with three equivalents of benzaldehyde; and cyclizing with scandium triflate, thereby obtaining said tri-functionalized cryptophane. In an exemplary embodiment, the intermediate is tris-(2-bromoethyl)cyclotriveratrylene and to the tri-functionalized cryptophane is tri-propargyl cryptophane.

In one embodiment, provided herein is a method of synthesizing a biosensor having increased affinity for a noble element, comprising the steps of: mediated by Cu(I), coupling a tri-functionalized cryptophane with an affinity tag; and complexing a hyperpolarized noble element with the tri-functionalized cryptophane coupled tag, wherein the tri-functionalized cryptophane comprises two cyclotriveratrylene (CTV) units and wherein a dipole moment exists between said first and second cyclotriveratrylene (CTV).

In another embodiment, provided herein is a method of detecting the activity of a α-carbonic anhydrase (CA) isozyme in a biological sample of a subject, comprising the step of contacting the biological sample with a biosensor comprising a hyperpolarized noble element complexed to a tri-functionalized cryptophane coupled affinity tag, wherein the affinity tag is specific to said α-carbonic anhydrase isoenzyme; and analyzing the signal in said element, whereby a signal indicates activity of said α-carbonic anhydrase isozyme.

In one embodiment, provided herein is a method of diagnosing a disease associated with α-carbonic anhydrase isoenzyme expression in a subject, comprising the step of obtaining a biological sample from said subject; contacting the biological sample with a biosensor comprising a hyperpolarized noble element complexed to a tri-functionalized cryptophane coupled affinity tag, wherein the affinity tag is specific to said α-carbonic anhydrase isoenzyme; analyzing the signal in said element; and comparing the signal obtained from the sample with a signal obtained under the same conditions in a standard.

In another embodiment, provided herein is a method for screening for a candidate agent capable of modulating the activity of a protein in a biological sample, comprising the step of contacting a first portion of the biological sample with a biosensor comprising a hyperpolarized noble element complexed to a tri-functionalized cryptophane coupled affinity tag, wherein the affinity tag is specific for the protein sought to be modulated and analyzing the signal of said element; contacting a second portion with the candidate agent screened; contacting the second portion with the same biosensor; and comparing the detected signal in the second portion, whereby a difference in the signal between the first and second portions indicates said agent being capable of modulating the activity of the protein. The term "signal," as used herein, refers to a signal detectable using nuclear magnetic resonance (NMR), magnetic resonance imaging (MRI), radiographic imaging, or other imaging modality. In one example, the signal is a chemical shift that can be detected by NMR.

In one embodiment, the biosensor of the invention is used in an in vivo application. In another embodiment, the biosensor of the invention is used in magnetic resonance imaging (MRI). In another embodiment, the biosensor of the invention is used in single photon emission computed tomography (SPECT). In another embodiment, the biosensor of the invention is used in positron emission tomography (PET). In another embodiment, the biosensor of the invention is used in any in vivo detection method known to one of skilled in the art. In another embodiment, the biosensor of the invention is used in an in vitro application. In another embodiment, the biosensor of the invention is used in an ex vivo application.

In another embodiment, the biosensor of the invention can be used to diagnose a disease, wherein the disease is associated with an organ or a tissue that can be accessed readily by the biosensor. In another embodiment, the biosensor of the invention can be used to diagnose a disease of lung, brain, or breast, where the biosensor can be readily delivered. Examples of a disease diagnosed by the biosensor of the invention include, but are not limited to, a cancer, a glaucoma, an epilepsy, a disease associated with α-carbonic anhydrase, an asthma, a stroke and a tuberculosis.

The invention relates, in one embodiment, to magnetic resonance imaging (MRI) biosensors with improved solubility and affinity to a noble element. In another embodiment, the invention relates to methods and systems for the detection of proteins using the chemical shift observed in a noble element complexed to the biosensor resulting from a change in the xenon local environment as the result of protein binding or enzyme activity.

Figure 9:
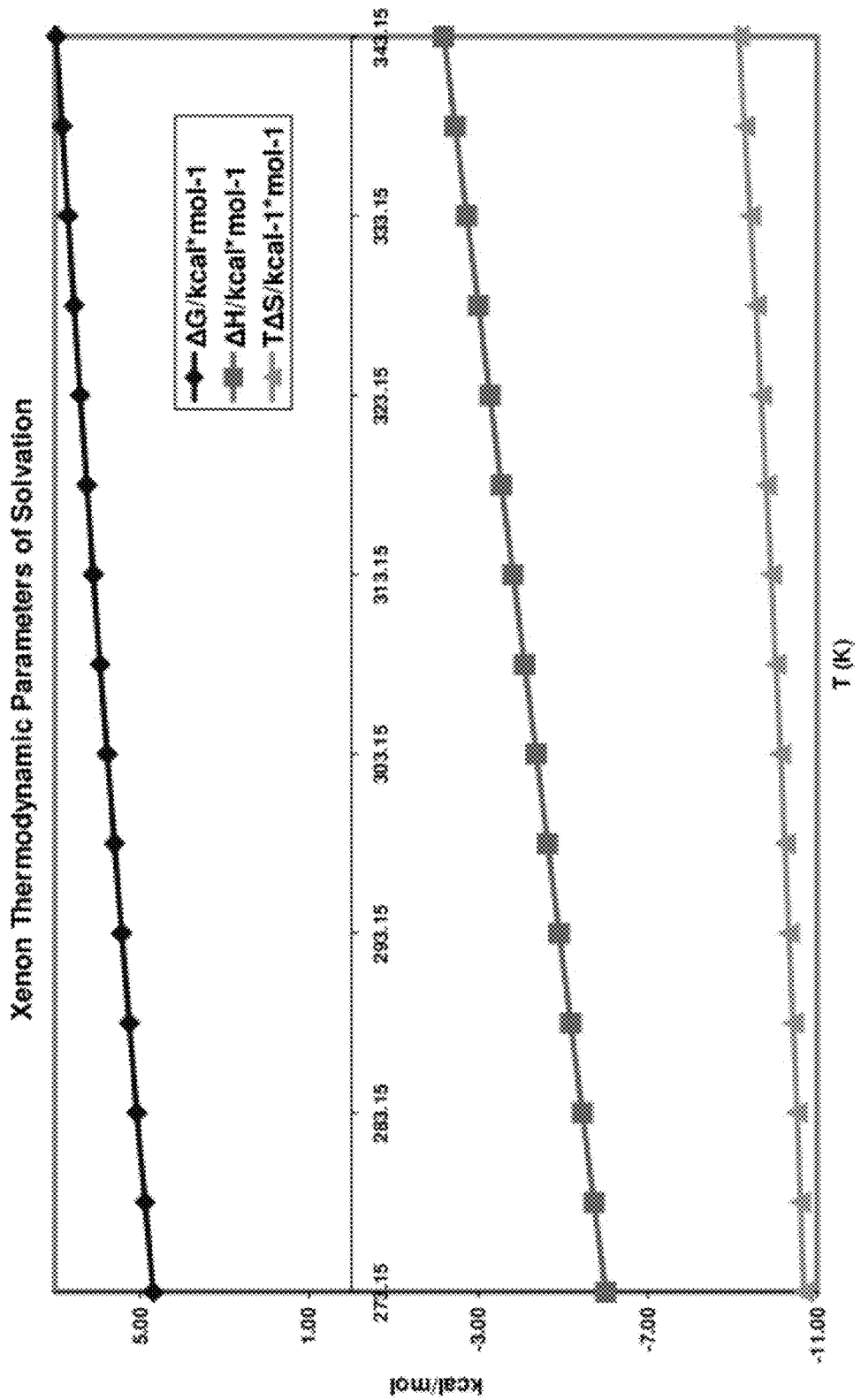
FIG. 9 shows trends in xenon solvation energy.

In one embodiment, provided herein is a new cryptophane-A derivative functionalized with three acetic acid groups that was synthesized. In another embodiment, tricarboxylate cryptophane was determined by isothermal titration calorimetry (ITC) and fluorescence quenching assay to have a xenon association constant of 33,000 $M^{-1}$ at 293 K, which is the highest affinity for xenon measured for any host molecule to date. Fluorescence lifetime measurements of tricarboxylate cryptophane in the presence of varying amounts of xenon confirmed static quenching by the encapsulated xenon and the presence of a second conformer in solution. As would be readily understood by a person skilled in the art, the fact that the entropy term for binding xenon to the cages created by the two cyclotriveratrylene (CTV) units in water is favorable (negative), the binding affinity for xenon improves as the temperature increases (going from rt to 37° C., physiological temp). (See also Table 2 and FIG. 9). Therefore, in one embodiment, the xenon 33,000 M$^{-1}$ association constant at 293 K increases to about to 50,000 M$^{-1}$ at 310 K.

In one embodiment, acid-base titrations and aqueous nuclear magnetic resonance (NMR) spectroscopy of tricarboxylate cryptophane and a previously synthesized tri-triazole propionate cryptophane (TTPC) show how the steric bulk of the cryptophane core and solvation of carboxylate anions affect in one embodiment, the aqueous behavior of the molecule. In one embodiment, the crown-saddle (CS) conformer of tricarboxylate cryptophane is detectable in aqueous solution, whereas only the crown-crown (CC) conformer of tri-triazole propionate cryptophane is observed.

In another embodiment, provided herein is the construction of target-specific xenon biosensors wherein the trifunctionalizing procedure described herein enables the resultant molecule to have substituents that enhance solubility of the sensors provided herein in up to three positions, while one or two positions in certain embodiments, are reserved for specific targeting or attachment of fluorophores or radiolabels. In one embodiment, xenon is a better fluorescence quencher of tri-acetic acid (TAAC) than tri-triazole propionate cryptophane (TTPC), based on the longer fluorescence lifetime of TAAC, and longer timescale for collisional quenching. In another embodiment, xenon is a poor fluorescence quencher in these systems, despite the fact that it occupies almost half the volume of the cryptophane cavity, and in certain embodiments collides, on average, hundreds of times with each chromophore before the $S_1 \rightarrow S_0$ electronic transition occurs from the one excited 1,2-dialkoxybenzene molecule in the cryptophane.

In one embodiment, the hyperpolarized noble element used in the biosensors described herein, which are used in the methods provided herein is Xe or any of its radioactive isotopes. Accordingly in one embodiment the isotope of xenon used in the biosensors described herein, used in the methods provided is $^{110}$Xe, or $^{111}$Xe, $^{112}$Xe, $^{113}$Xe, $^{114}$Xe, $^{115}$Xe, $^{116}$Xe, $^{117}$Xe, $^{118}$Xe, $^{119}$Xe, $^{120}$Xe, $^{121}$Xe, $^{122}$Xe, $^{123}$Xe, $^{124}$Xe, $^{125}$Xe, $^{126}$Xe, $^{127}$Xe, $^{129}$Xe, $^{131}$Xe, $^{132}$Xe, $^{133}$Xe, $^{133}$Xe, $^{134}$Xe, $^{135}$Xe, $^{135}$Xe, $^{137}$Xe, $^{138}$Xe, $^{139}$Xe, $^{140}$Xe, $^{141}$Xe, $^{142}$Xe, $^{143}$Xe, $^{144}$Xe, $^{145}$Xe, $^{145}$Xe, $^{146}$Xe, $^{147}$Xe or their combination in other discrete embodiments.

The xenon biosensor described herein may be used in any suitable imaging technique known to one of skilled in the art for detecting various diseases or conditions (e.g., tumor). Examples of imaging techniques may include, but are not limited to, magnetic resonance imaging (MRI), positron emission tomography (PET), and single photon emission computed tomography (SPECT).

Current limitations in developing $^{129}$Xe MRI contrast agents for in vivo studies include the difficulties of synthesizing large quantities of functionalized cryptophanes and delivering laser-polarized $^{129}$Xe to living tissue. Improved methods for synthesizing xenon biosensors are crucial to developing this technology for in vivo applications. Because the lifetime of hyperpolarized $^{129}$Xe is relatively short in biological fluids, in one embodiment hyperpolarized $^{129}$Xe is continuously or repeatedly delivered to the site of the cryptophane, thereby maintaining signal intensity. Thus, in one embodiment, xenon biosensors described in the systems, methods and kits described herein utilize $^{129}$Xe MR spectroscopic identification of biomarkers in the lungs, where hyperpolarized xenon could be delivered through semi-continuous inhalation. In another embodiment, for application in less accessible target areas, such as the breast, hyperpolarized xenon and said biosensors are delivered through direct injection. Xenon gas (specifically $^{127}$Xe and $^{133}$Xe) may also be used in other imaging techniques, for example, SPECT.

$^{127}$Xe decays by electron capture with a 36.4-d half-life. The principal gamma emissions and abundances are: 172 keV (25%); 203 keV (68%); and 375 keV (18%). These photons are known to provide better intrinsic spatial resolution. Thus, in another embodiment, xenon biosensors described in the systems, methods and kits described herein utilize $^{127}$Xe for detecting various diseases or conditions using SPECT imaging.

$^{133}$Xe also diffuses easily, passing through cell membranes and exchanging freely between blood and tissue. It is distributed in the lungs in a manner similar to that of air, thus representing the regions of the lung that are aerated. The gamma photons of $^{133}$Xe can then be employed to obtain counts per minute per lung or region of the lung, or to display their distribution as a scan. $^{133}$Xe is used to assess and evaluate pulmonary function and to provide to images of the lungs in both cardiac and pulmonary diseases, such as asthma, pulmonary emphysema, bronchiectasis, carcinoma of the lung, and pulmonary embolism. $^{133}$Xe is also used to assess and evaluate regional cerebral blood flow, mainly in patients with cerebrovascular disease. $^{133}$Xe has a half-life of approximately 5.2 days. Thus, in another embodiment, xenon biosensors described in the systems, methods and kits described herein utilize $^{133}$Xe for detecting various diseases or conditions. $^{133}$Xe may be used for SPECT in vivo imaging using suitable imaging techniques known to one of skilled in the art.

In one embodiment, provided herein is a biosensor comprising a hyperpolarized noble element complexed with a tri-functionalized cryptophane, wherein the tri-functionalized cryptophane is comprised of a first and second cyclotriveratrylene (CTV) unit having a dipole moment therebetween. In another embodiment, the biosensor comprising a hyperpolarized noble element is complexed with at least one affinity tag coupled to a tri-functionalized cryptophane, wherein the affinity tag is a target-specific tag and whereby reaction between the affinity tag and the target induces change in the chemical environment of the noble element resulting in a detectable chemical shift.

In another embodiment, provided herein is a method of synthesizing a biosensor having increased affinity for a noble element, comprising the steps of: mediated by Cu(I), coupling a tri-functionalized cryptophane with an affinity tag; and complexing a hyperpolarized noble element with the tri-functionalized cryptophane coupled tag, wherein the tri-functionalized cryptophane is comprised of two cyclotriveratrylene (CTV) units and wherein a dipole moment exists between said first and second cyclotriveratrylenes (CTVs).

In one embodiment, the terms "hyperpolarize", "polarize", and the like are used interchangeably and mean to artificially enhance the polarization of certain noble gas nuclei over the natural levels at thermal equilibrium. Such an increase is desirable in other embodiments because it allows stronger signals corresponding to better NMR images and spectroscopy signals of the gas in the body. As is known by those of skill in the art, hyperpolarization can be induced in one embodiment by spin-exchange with an optically pumped alkali-metal vapor or by metastability exchange in another embodiment.

In one embodiment, the term "chemical shift" refers to circumstances whereby, for a Xe-129 atom having a particular NMR resonance frequency within a cryptophane or related to organic cage which shields the xenon nucleus from the external magnetic field to a certain extent, a change in the environment of the cryptophane cage will result in a change of the ability of the cryptophane to shield the xenon from the magnetic field. The resulting shift of the NMR resonant frequency, in one embodiment, is referred to as a "chemical shift" and the degree of shielding depends on the degree to which the very polarizable xenon nucleus is perturbed within a given cryptophane. In one embodiment, the xenon biosensor may be used as SPECT agents, by taking advantage of the very high signal (from radioactive xenon isotopes) per nucleus to identify rare species in vivo. In some embodiments, by targeting many xenon nuclei to a tumor, for example, target molecules can be detected and the tumor may also be detected at an early stage.

In one embodiment, the reaction of the affinity tags, which are coupled to the tri-functionalized cryptophane, used in the systems, methods and kits described herein by the corresponding targets described herein, induces change in the ability of the tri-functionalized cryptophane to shield the complexed hyperpolarized noble element from the applied magnetic field, resulting in a chemical shift that is detectable by NMR; and is specific to the target sought to be detected.

In one embodiment, the term "affinity tag" refers to any substituent that can be covalently attached to the tri-functionalized cryptophane moieties of cyclotriveratrylene comprising the cage in which the noble element is enclosed, capable of reacting with a target compound and inducing change in the microenvironment of the biosensors, thereby inducing a change of resonant frequency of the noble element entrapped between the two tri-functionalized cryptophane moieties of cyclotriveratrylene. In one embodiment, the affinity tag is an enzyme substrate, or a folate, a glucose moiety, a peptoid, a small molecule, a peptide such as RGD or their combination in other discrete embodiments of the affinity tags used in the biosensors and methods described herein.

In one embodiment, the term "substrate" refers to a substance acted upon by an enzyme in a biochemical reaction. After the biochemical reaction, at least one product is generated due to the action of the enzyme on the substrate. A "soluble substrate" refers in another embodiment, to a substrate which is not membrane bound. The term "enzyme" refers to any protein that catalyzes a biochemical reaction. Proteins having non-amino-acid to modifications such as glycosylation or containing other non-proteinaceous components such as metal ion prosthetic groups are included within this definition.

In one embodiment, the affinity tag is folate (5-methyltetrahydropteroylglutamate) and the target sought to be imaged is any cell that overexpressed the folate binding protein (FBP) or has a high level of cell-surface folate receptors. Many cancer cells upregulate folate receptor relative to healthy cells, which makes folate a useful targeting moiety.

In another embodiment, the term "protein" or "polypeptide" or "peptide" is used in its broadest sense to refer to a compound of two or more subunit amino acids, amino acid analogs, or other peptidomimetics. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If in another embodiment, the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation and the like. In another embodiment, as ionizable amino and carboxyl groups are present in the molecule, a particular polypeptide may be obtained as an acidic or basic salt, or in neutral form. In one embodiment, a polypeptide may be obtained directly from any source organism, or may be recombinantly or synthetically produced.

In one embodiment, the term "specific", in reference to the binding of two molecules or a molecule and a complex of molecules, refers to the specific recognition of one for the other and the formation of a stable complex, as compared to substantially less recognition of other molecules and the lack of formation of stable complexes with such other molecules. In another embodiment, "specific", in reference to binding, means that to the extent that a molecule forms complexes with other molecules or complexes, it forms at least fifty percent of the complexes with the molecule or complex for which it has specificity. In one embodiment, the molecules or complexes have areas on their surfaces or in cavities giving rise to specific recognition between the two binding moieties. Exemplary of specific binding are antibody-antigen interactions, enzyme-substrate interactions, polynucleotide hybridizations and/or formation of duplexes, cellular receptor-ligand interactions, and so to forth in other embodiments.

In one embodiment, the affinity tags used in the biosensors described herein, which, in certain embodiments are used in the methods provided herein, are specific for cathepsins, matrix metalloproteinases (MMPs), glucose transporters, somatostatin receptor, etc. A person skilled in the art would readily recognize that many targets have a target-specific affinity tag which is capable of being attached to the tri-functionalized cryptophane molecules described herein.

In one embodiment, the hyperpolarized noble element used in the biosensors utilized in the systems, methods and kits provided herein, is xenon, or in another embodiment, an isotope of xenon. An isotope of xenon, xenon-129, has non-zero nuclear spin (i.e., $I=\frac{1}{2}$) and therefore is a nucleus which, in one embodiment, is suited to study by nuclear magnetic resonance techniques. The nuclear magnetic resonance signals obtainable from $^{129}Xe$ are extraordinarily sensitive to local environment and therefore very specific to environment.

In another embodiment, xenon interacts with proteins and lipids in plasma, which reduces the contribution of entropy ($T\Delta S|_{P,c}=0.12$) relative to Xe binding of triacetic acid-functionalized cryptophane (TAAC) in buffer.

In another embodiment, the $^{129}Xe$ isotope is, in principle, suited to NMR uses, but is 26% naturally abundant and has a sensitivity relative to $^1H$ (in conventional NMR) of $2.12 \times 10^{-2}$. In another embodiment, the resonance frequency of $^{129}Xe$ spans an enormous range (0-300 ppm) over the gas and condensed phase, and is exceptionally sensitive to chemical environment. Its longitudinal relaxation time, $T_1$, is huge (practically at least 3000 s in the pure gas phase, and theoretically perhaps as long as 56 hrs at 1 atm, and is particularly sensitive to chemical environment, $O_2$ concentration, and the effects of other relaxation promoters. Its transverse relaxation time is also susceptible to relaxation promoters.

Noble gases may be hyperpolarized for use in one embodiment, through any of various means known in the art, such as spin-exchange interactions with optically pumped alkali metal vapor. The optical pumping and spin-exchange can be performed in the absence of an applied magnetic field, or in another embodiment, using modest fields of about 1 G or larger. Pumping in the NMR magnet bore at fields of several Tesla is also possible. The maximum steady-state $^{129}Xe$ nuclear polarization achievable depends in certain embodiments, to on the time constant characterizing the spin exchange with the alkali metal and the time constant characterizing the relaxation ($T_1$) due, in an embodiment, to contact with the surfaces of the pumping cell. In another embodiment, with $T_1$ of 20 min, polarizations of 20-40% are practicable, and polarizations of 70% or more are attainable in other embodiments. The long $T_1$ of the gas allows in one embodiment for samples to be manipulated, even stored as Xe ice, and transported on time scales of hours or even days, without serious loss of magnetization.

In another embodiment, TAAC exhibits higher affinity for xenon than any known host molecule. The agreement between the fluorescence quenching and ITC data validates in one embodiment the use of both techniques for the determination of xenon binding constants. The additional stabilization of −0.37 kcal/mol of the Xe@TAAC complex relative to Xe@TTPC demonstrates in one embodiment, that differently functionalized cryptophane cores lead to different xenon binding affinities. In one embodiment, introducing ionizable groups close to the cryptophane that create a molecular dipole moment along the cavity leads to improvements in xenon binding. Accordingly and in one embodiment, the functionalizing moieties used in the biosensors and methods described herein, are selected based on their ability to create the optimal dipole moment for the imaging target. In another embodiment, increasing the dipole moment of the cryptophane cage (and xenon affinity) used in the biosensors described herein which, in other embodiments are utilized in the methods described herein, is done by introducing heteroatoms within the cage. In one embodiment nitrogen and sulfur atoms were incorporated into the tri-functionalized cryptophane cages, which should in certain embodiments improve xenon binding.

In one embodiment, the term "dipole moment" refers to an asymmetric charge distribution inside a neutral molecule. The dipole moment is considered to be the product of the magnitude of the charges multiplied by the distance of separation between the charges. Dipole moment is measured in units of Debye. In the vapor phase, the water molecule, for example, has a dipole moment of 1.84 Debye. In another embodiment, the dipole moment between the two CTV units used in the biosensors and which are utilized in the methods described herein, have a dipole moment between about 3 and about 30 Debye.

In one embodiment, there are two or three affinity tags coupled to the tri-functionalized cryptophane used in the biosensors utilized in the methods described herein. In certain embodiments, when more than one affinity tag is coupled to the tri-functionalized cryptophanes described herein, these affinity tags could be the same or different. Accordingly and in one embodiment, the tri-functionalized cryptophanes used herein comprise a substrate as an affinity tag as well as two antibodies, specific for the enzyme corresponding to the coupled substrate. In another embodiment, the affinity tag is three benzenesulfonamide substituents.

The term "functionalized" refers in one embodiment to the modification of the cyclotriveratrylene (CTV) moieties with chemical groups that impart target functional properties and the process of attaching such groups is defined as "functionalization". In one embodiment, triphenol cryptophane is functionalized by reacting it with a triazole propionate radical, thereby obtaining a tritriazole propionate cryptophane (TTPC). In another embodiment, the cyclotriveratrylene (CTV) moiety functionalized with tritriazole propionate, combined with a cyclotriveratrylene (CTV) moiety functionalized with tricarboxylate, thereby creating a dipole moment between the CTV moieties, allowing for a higher affinity to $^{129}$Xe, which is substantially (more than 4-fold) higher than a monopropargyl cryptophane-A enclosed Xe. In one embodiment, the tri-functionalized cryptophane comprising the biosensors described herein and used in the methods provided herein, is functionalized with a triazole propionate moiety, acetic acid moiety, long-chain PEG, amines, amides, sulfones, esters, peptides, sugars, polymers, or their combination of polar, water-solubilizing groups that are neutral, positively or negatively charged in water.

Accordingly and in one embodiment, provided herein is a method of synthesizing a tri-functionalized cryptophane, comprising the steps of: in the presence of DMF, deprotonating cyclotriveratrylene (CTV), using cesium carbonate and reacting the deprotonated cyclotriveratrylene with 2-[3-allyloxy-4-(2-iodo-ethoxy)-benzyloxy]-tetrahydropyran yielding 2,7,12-tris[2-[4-(hydroxymethyl)-2-propargyloxyphenoxy]ethoxy]-3,8,13-trimethoxy-10,15-dihydro-2H-tribenzo[a,d,g]cyclononene; in the presence of an organic solvent, cyclizing the resulting 2,7,12-tris[2-[4-(hydroxymethyl)-2-propargyloxyphenoxy]ethoxy]-3,8,13-trimethoxy-10,15-dihydro-2H-tribenzo[a,d,g]cyclononene, obtaining triallyl-cryptophane; deprotecting the triallyl-cryptophane using a catalyst, thereby obtaining triphenol-cryptophane; alkylating the triphenol-cryptophane using a functionalizing molecule in the presence of cesium carbonate in DMF, thereby obtaining triester-cryptophane, whereby the triester is of the functionalizing molecule; and saponifying the triester-cryptophane in tetrahydrofuran using potassium hydroxide thereby obtaining a triacid cryptophane. In one embodiment, the biosensors described herein comprise the tri-functionalized cryptophane made by the methods described herein.

Figure 23:
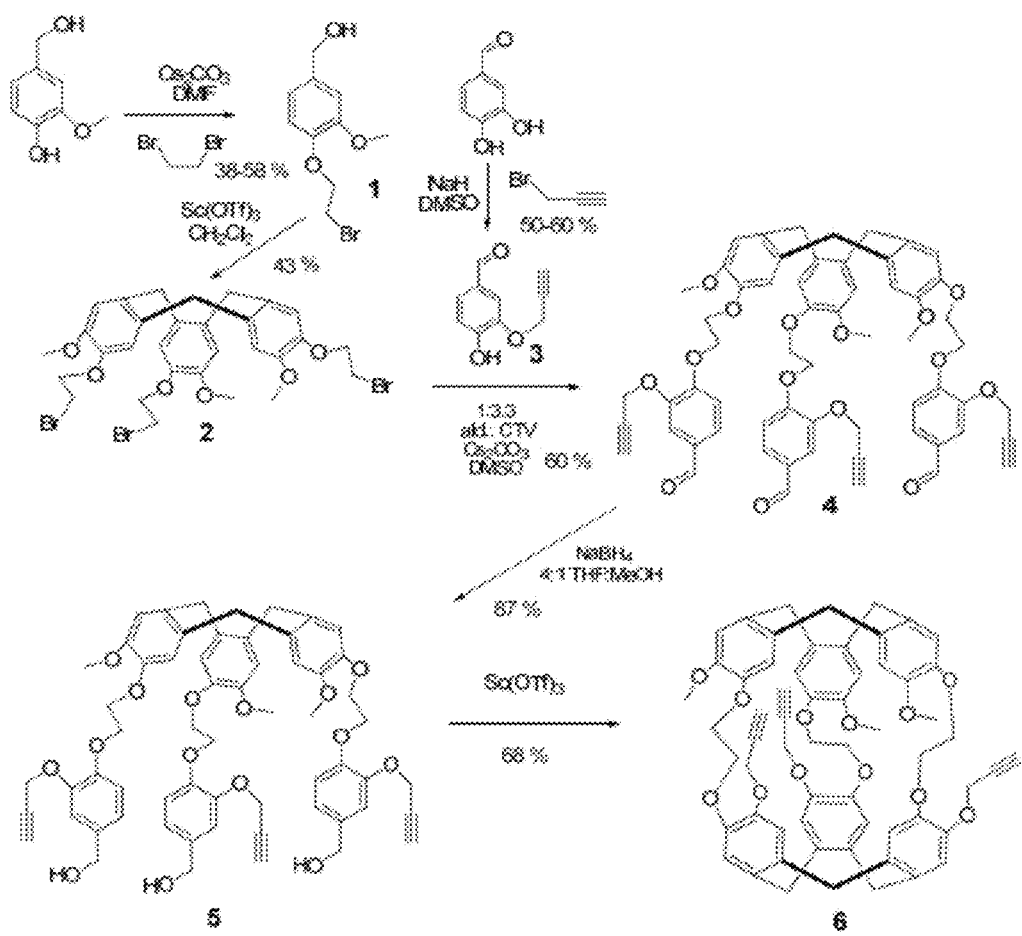
FIG. 23 shows six non-linear steps to synthesize tri-propargyl cryptophane.

In another embodiment, provided herein is a method for synthesizing a tri-functionalized cryptophane, comprising the steps of: obtaining a functionalized cyclotriveratrylene (CTV) intermediate by a process that eliminates the need for allyl group protection or deprotection; reacting said intermediate with three equivalents of benzaldehyde; and cyclizing with scandium triflate, thereby obtaining said tri-functionalized cryptophane. The process that eliminates the need for allyl group protection or deprotection is well known in the art. For example, FIG. 23 shows trimerization of compound 1 to yield tris-(2-bromoethyl)cyclotriveratrylene. This process eliminates the need for allyl group protection or deprotection. In one embodiment, the intermediate is tris-(2-bromoethyl) cyclotriveratrylene and the tri-functionalized cryptophane is tri-propargyl cryptophane.

In one embodiment, with the methods described herein a water-soluble TTPC is synthesized, which has better Xe binding, $K_A \approx 30,000$ M$^{-1}$ at 310 K, than any previously described compound that is not tri-functionalized using the methods described herein.

In another embodiment, provided herein is a method of synthesizing a biosensor having increased affinity for a noble element, comprising the steps of: mediated by Cu(I), coupling a tri-functionalized cryptophane with an affinity tag; and complexing a hyperpolarized noble element with the tri-functionalized cryptophane coupled tag, wherein the tri-functionalized cryptophane comprises first and second cyclotriveratrylene (CTV) units and wherein a dipole moment exists between said first and second cyclotriveratrylene (CTV).

In one embodiment, the biosensors provided herein, which are utilized in the methods described herein, are used to analyze the activity of target proteins. The carbonic anhydrase family (CA) refers to roughly 15 different catalytically active zinc metalloenzymes involved in the reversible hydration-dehydration of carbon dioxide: $CO_2 + H_2O \leftrightarrow HCO_3^- + H^+$. These molecules participate in a variety of physiological and biological processes with substantial diversity in tissue distribution, subcellular localisation, and biological functions. In another embodiment, carbonic anhydrase IX (CAIX) is overexpressed in transformed cell lines and in several human malignancies and is recognised as a tumour associated antigen and linked to the development of human cancers. In one embodiment, CAIX expression correlates positively in several cancers, with levels of hypoxia in tumours. In yet other embodiments, overexpression of CAIX is associated with a poor prognosis in lung, breast, and cervical cancer patients. In another embodiment, indanesulfonamides or its derivative in certain embodiments, is an inhibitor of several CA isoenzymes.

Accordingly and in one embodiment, provided herein is a method of analyzing the activity of a α-carbonic anhydrase (CA) isoenzyme in a biological sample of a subject, comprising the step of contacting the biological sample with a biosensor comprising a hyperpolarized noble element complexed to a tri-functionalized cryptophane coupled affinity tag, wherein the affinity tag is specific to said α-carbonic anhydrase isoenzyme; and analyzing the chemical shift in said element, whereby a chemical shift indicates activity of said α-carbonic anhydrase isoenzyme. In another embodiment, the biosensor comprises a cryptophane having one or more triazole propionate functionalizing moieties and an indanesulfonamide derivative affinity tag coupled thereto. In one embodiment, the indanesulfonamide derivative used as the affinity tag for the biosensor described herein, is benzenesulfonamide, or acetazolamide, methazolamide, ethoxzolamide, dichlorophenamide, dorzolamide and brinzolamide or their combination in other discrete embodiments.

In one embodiment, the biological sample contacted by the biosensors described herein, utilized in the methods provided herein is blood, or sputum, sera, urine, mucosa, feces, epidermal sample, skin sample, cheek swab, sperm, semen, amniotic fluid, cultured cells, bone marrow sample, chorionic villi, primary tumor biopsies, metastases biopsies, diffuse tumor biopsies, or a combination thereof in other discrete embodiment of the biological samples used. In one embodiment, the primary tumor biopsies, or metastatic biopsy in another embodiment, is taken from lung, breast, and cervical cancer patients.

In one embodiment, provided herein is a method of diagnosing a disease associated with α-carbonic anhydrase isoenzyme expression in a subject, comprising the step of obtaining a biological sample from said subject; contacting the biological sample with a to biosensor comprising a hyperpolarized noble element complexed to a tri-functionalized cryptophane coupled affinity tag, wherein the affinity tag is specific to said α-carbonic anhydrase isoenzyme; analyzing the chemical shift in said element; and comparing the chemical shift obtained from the sample with a chemical shift obtained under the same conditions in a standard. In one embodiment, the standard is taken from a subject or pool of subjects correctly diagnosed with a disease associated with α-carbonic anhydrase isoenzyme expression.

Accordingly and in one embodiment, provided herein is a method of diagnosing, or in another embodiment, providing a prognosis on the development of gastric cancer in a subject, comprising the step of contacting a gastric biopsy from the subject with a biosensor comprising $^{129}Xe$ complexed to TTPC coupled affinity tag, wherein the affinity tag is benzenesulfonamide, acetazolamide, methazolamide, ethoxzolamide, dichlorophenamide, dorzolamide brinzolamide or their combination; analyzing the chemical shift in said $^{129}Xe$; and comparing the chemical shift obtained from the gastric biopsy with a chemical shift obtained under the same conditions in a standard. In one embodiment, the standard is taken from a subject or pool of subjects correctly diagnosed with a gastric cancer following the determination of reduced expression of CAIX.

In one embodiment, the methods of producing the biosensors provided herein, are used in the compositions and methods described herein for detection and diagnosis of cancer in a subject as described herein. Accordingly and in one embodiment, provided herein is an in-vivo cancer cell detection system comprising: a detectably labeled biosensor wherein said biosensor comprises: a hyperpolarized noble element; complexed with a tri-propargyl-cryptophane-A coupled to one or more azido-peptides, wherein the peptide is capable of binding an integrin and whereby cellular uptake of the biosensor bound to the integrin by the cancer cell is detectable.

In another embodiment, the term "Integrins", refers to a family of transmembrane adhesion receptors that are principal mediators of cell attachment, migration, differentiation, and survival. Structurally, integrins are heterodimeric receptors that are composed of large extracellular domains, one transmembrane helix, and small intracellular domains for each subunit. These receptors consist of an α- and a β-subunit, which associate non-covalently in defined combinations. To date, 18 α-subunits and 8 β-subunits have been identified, which to associate selectively to form at least 24 integrins. In certain embodiments, integrins transduce messages via various signaling pathways and influence proliferation and apoptosis of tumor cells, as well as of activated endothelial cells. Unique combination of integrins on the cell surface allows in other embodiments, for cells to recognize and then respond to a variety of extracellular ligands. Integrin $\alpha_v\beta_3$ is a prominent member of the integrin family. It has been implicated in the pathophysiology of malignant tumors where it is required for tumor angiogenesis and is highly expressed on both endothelial cells in neovasculature and highly aggressive human carcinomas. In another embodiment, integrin $\alpha_v\beta_3$ mediates adhesion of tumor cells on a variety of extracellular matrix proteins, allowing these cells to migrate during invasion and extravasation. In breast cancer, $\alpha_v\beta_3$ characterizes the metastatic phenotype, as this integrin is upregulated in invasive tumors and distant metastases. The $\alpha_v\beta_3$ receptor binds to a variety of extracellular matrix proteins, including fibrinogen, fibronectin, osteopontin, thrombospondin, and vitronectin largely through interaction with the Arg-Gly-Asp (RGD) tripeptide sequence. In one embodiment, the affinity tag peptide employed in the biosensors used in the methods and compositions described herein, is a di-, tri-, tetra-RGD peptide, a cyclic RGD peptide, or a combination thereof.

Accordingly and in one embodiment, provided herein is an in-vivo cancer cell detection system comprising: a detectably labeled biosensor wherein said biosensor comprises: a hyperpolarized noble element complexed to a tri-functionalized cryptophane coupled affinity tag, wherein the affinity tag is peptide, which is capable of binding an integrin and whereby cellular uptake of the biosensor bound to the integrin by the cancer cell is detectable, wherein the peptide is tetra-RGD. In another embodiment, the peptide is tri-RGD. In another embodiment, the peptide is di-RGD. In related embodiments, the peptide is a linear RGD-containing or cyclic RGD-containing peptide.

In another embodiment, integrin $\alpha_v\beta_3$ is implicated in multiple aspects of tumor progression, metastasis, and osteoclast bone resorption. Many tumors have high expression of $\alpha_v\beta_3$, and this expression correlates with tumor progression in melanoma, glioma, ovarian, prostate, breast cancer, as well as other cancers. In another embodiment, the $\alpha_v\beta_3$ receptor is used as a therapeutic target for novel anticancer agents. Accordingly, the methods provided herein can be readily used to evaluate the efficacy of drugs targeting the $\alpha_v\beta_3$ receptor.

Likewise and in another embodiment, provided herein is a method of imaging a to cancer in vivo in a subject, comprising the step of contacting a suspected cancer cell with a composition comprising a detectably labeled biosensor wherein said biosensor comprises: a hyperpolarized noble element; complexed with a tri-functionalized cryptophane coupled peptide, wherein the peptide is capable of binding an integrin expressed on the surface of the pancreatic or lung cell and analyzing the change in fluorescent intensity of the suspected cell before and after administration of the composition, whereby increase in fluorescent intensity, indicates the cell is cancerous. In one embodiment, the increase in expression of $\alpha_v\beta_3$ correlates with progression of the cancer, or in another embodiment with onset of metastases. In certain embodiments, the methods of imaging cancer in-vivo described herein are used for staging cancer.

In one embodiment, the tri-functionalized cryptophane biosensors described herein do not have an affinity tag and are used as a general MR contrast agent, wherein the increased solubility imparted by the functionalizing of the molecule and its increased affinity to the noble element, increases the signal-to-noise ratio observed. The non-tagged biosensors thus described, can be used in certain embodiments to image cancer or other pathologies where noble element solubility is limited by solubility. In one embodiment, the tri-functionalized cryptophane biosensors described herein, obviates the need for attaching chiral (e.g. peptides in certain embodiments) moieties to the cryptophane cage, which when attached, produce diastereomers. This is since the tri-functionalized cryptophane itself is chiral, and exists as a racemic mixture of enantiomers, unless it is synthesized in enantiomerically pure form. Diastereomers such as peptide-containing cryptophanes, are different compounds, which produce different Xe-129 NMR chemical shifts, make it more difficult to interpret the Xe-129 NMR spectrum, and lead to lower S/N as the signal is spread out amongst many peaks.

In one embodiment, the mono-, di-, tri- or tetra-RGD peptides used as the affinity tag in the compositions and methods described herein, are capable of binding integrins other than the $\alpha_v\beta_3$ integrin and the methods of imaging cancer in-vivo in a subject described herein, or in another embodiment, the methods of evaluating the efficacy of cancer drug therapy Described herein, or in another embodiment, the methods of detecting a cancer cell in-vivo, are effected through interactions with non-$\alpha_v\beta_3$ integrins. In one embodiment, the integrins are $\alpha_1\beta_1$, $\alpha_5\beta_1$, $\alpha_v\beta_3$, and $\alpha_6\beta_4$ (coupled to the Ras-extracellular signal-regulated kinase (ERK) to signaling pathway by the adaptor protein Shc), $\beta_{1C}$ integrin (an unspliced form of the integrin $\beta_1$ subfamily), and others that are now known or later discovered, whose expression or function in cells enables the modulation of the function of those integrins.

In another embodiment, the term "labeled" refers to the attachment of a moiety, capable of detection by spectroscopic, radiologic or other methods, to the biosensors provided herein. In one embodiment, the label used in the methods and compositions provided herein, is Cy3 dye. In another embodiment, the label is dinitrophenyl, fluorescein and derivatives thereof, rhodamine, derivatives of rhodamine, phycoerythrin, phycocyanin, allophycocyanin, o-phthaldehyde and fluorescamine, Texas red, rhodamine green, Oregon green, Cascade blue, phycoerythrin, Cy3, Cy5, Cy2, Cy7, coumarin, infrared 40, MR 200, IRD 40, green fluorescent protein and combinations thereof.

In another embodiment, provided herein is a method for screening for a candidate agent capable of modulating the activity of a protein in a biological sample, comprising the step of contacting a first portion of the biological sample with a biosensor comprising a hyperpolarized noble element complexed to a tri-functionalized cryptophane coupled affinity tag, wherein the affinity tag is specific for the protein sought to be modulated and analyzing the chemical shift of said element; contacting a second portion with the candidate agent screened; contacting the second portion with the same biosensor; and comparing the detected chemical shift in the second portion, whereby a difference in the chemical shift between the first and second portions indicate an agent capable of modulating the activity of the protein. In one embodiment, the proteins' activity sought to be modulated using the candidate agents screened using the methods and biosensors described herein, is an enzyme, an antibody, an aptamer, a peptoid, a receptor, or a combination thereof.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, to cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Reagents

Organic reagents and solvents were used as purchased from the following commercial sources: Acros: cesium carbonate, anhydrous dimethylsulfoxide (DMSO), anhydrous dimethylformamide (DMF), $d_6$-DMSO, CDCl$_3$, 4-hydroxy-3-methoxybenzylalcohol, triphenylphosphine, 1,2 dibromoethane, sodium borohydride, 10% palladium on carbon, 3,4-dihydroxybenzaldhyde, ethyl bromoacetate, palladium(II) acetate. Fisher: sodium chloride, potassium phosphate, ethyl acetate, dichloromethane, chloroform, hydrochloric acid, sodium hydroxide, sodium sulfate, acetone, hexanes, sodium iodide, potassium hydroxide. Cambridge Isotope Laboratories: deuterium oxide. Airco Industrial Gases: research grade xenon gas. Aldrich: $d_{12}$-mesitylene, 3,4-dihydro-2H-pyran, allyl bromide, pyridinium p-toluenesulfonate, sodium deuteroxide 40 wt. % in D$_2$O, diethylamine.

General Methods

All organic reactions were carried out under nitrogen atmosphere. $^1$H NMR (500.14 MHz) and $^{13}$C (125.77 MHz) spectra were obtained on a Bruker AMX 500 or DMX 600 spectrometer at the University of Pennsylvania NMR Facility. Spectra were referenced to TMS at 0.00 ppm in CDCl$_3$ or the residual solvent peak at 2.50 ppm in $d_6$-DMSO. Electrospray ionization (ESI) mass spectrometry was performed in low resolution mode on a Micromass LC Platform and in high resolution mode on a Micromass Autospec at the Mass Spectrometry Center in the Chemistry Department at the University of Pennsylvania. For fluorescence and ITC measurements in buffer, solutions were prepared with water deionized using Mar Cor Premium Grade Mixed Bed Service Deionization. Column chromatography was performed using 60 Å porosity, 40-75 μm particle size silica gel form Sorbent Technologies. Thin layer chromatography was performed using silica gel plates with UV light at 254 nm for detection.

2,7,12-Tris(2-{2-allyloxy-4-[tetrahydro-pyran-2-yloxymethyl]-phenoxyl}-ethoxy)-3,8,13-trimethoxy-10,15-dihydro-5H-tribenzo[a,d,g]cyclononene 2-[3-allyloxy-4-(2-iodo-ethoxy)-benzyloxy]-tetrahydro-pyran (1.460 g, 3.575 mmol) and cesium carbonate (6.98 g, 21.45 mmol) were added to an oven-dried flask with stir bar and purged with nitrogen gas. Dry DMF (150 mL) was added by syringe and the mixture was allowed to stir for 30 min at rt. Cyclotriveratrylene (5.981 g, 14.30 mmol) was then added and the reaction was placed in a 55° C. oil bath with stirring overnight. The reaction was poured into saturated NaCl (600 mL), and extracted 3 times with $Et_2O$ (300 mL). The combined organics were washed 5 times with saturated NaCl (300 mL), dried over $Na_2SO_4$, and evaporated under reduced pressure. The crude material was then pumped under high vacuum to remove any residual DMF and purified by column chromatography ($CH_2Cl_2 \rightarrow 90:10$ $CH_2Cl_2$:acetone) to yield 2.74 g (60% yield) of 2,7,12-Tris(2-{2-allyloxy-4-[tetrahydro-pyran-2-yloxymethyl]-phenoxyl}-ethoxy)-3,8,13-trimethoxy-10,15-dihydro-5H-tribenzo[a,d,g]cyclononene as a clear glass. $^1$H NMR ($CDCl_3$) $\delta$=6.98 (s, 3H, aryl), 6.94-6.87 (m, 9H, aryl), 6.83 (s, 3H, aryl), 6.04 (m, 3H, allyl), 5.38 (m, 3H, allyl), 5.22 (m, 3H, allyl), 4.73 (d, 3H, $H_{ax}$, J=13.6 Hz), 4.69 (d, 3H, Ph-$CH_2$—O, J=11.8 Hz), 4.67 (t, 3H, THP), 4.59 (d, 6H, allyl), 4.38 (d, 3H, Ph-$CH_2$—O, J=11.8 Hz), 4.35 (m, 12H, O—$CH_2$—$CH_2$—O), 3.91 (m, 3H, THP), 3.74, (s, 9H, O—$CH_3$), 3.53 (m, 3H, THP), 3.53 (d, 3H, $H_{eq}$, J=13.5 Hz), 1.88-1.49 (m, 18H, THP). $^{13}$C NMR ($CDCl_3$) $\delta$=148.62, 148.51, 148.08, 146.79, 133.44, 132.91, 131.81, 131.74, 120.87, 117.27, 116.64, 114.62, 114.50, 114.01, 97.38, 69.92, 68.40, 68.21, 67.90, 61.99, 56.12, 36.18, 30.47, 25.35, 19.30. HRMS calcd for $C_{75}H_{90}O_{18}$ (M+Na$^+$) 1301.6025. found 1301.6015.

Tri-Allyl Cryptophane 2,7,12-Tris(2-{2-allyloxy-4-[tetrahydro-pyran-2-yloxymethyl]-phenoxyl}-ethoxy)-3,8,13-trimethoxy-10,15-dihydro-5H-tribenzo[a,d,g]cyclononene (560 mg, 0.39 mmol) was dissolved in 250 mL $CHCl_3$ and 250 mL formic acid was added with magnetic stirring. The reaction was purged with $N_2$ before being heated to reflux for 9 h. The solvent was then evaporated under reduced pressure. Toluene was added to the crude material and evaporated under reduced pressure to remove residual formic acid. The crude material was then purified by column chromatography ($CH_2Cl_2 \rightarrow CH_2Cl_2$:diethyl ether 90:10) to yield 152 mg 6 in 40% yield. $^1$H NMR ($CDCl_3$) $\delta$=6.76 (s, 3H, aryl), 6.74 (s, 3H, aryl), 6.72 (s, 3H, aryl), to 6.67 (s, 3H, aryl), 6.05 (m, 3H, allyl), 5.45 (m, 3H, allyl), 5.34 (m, 3H, allyl), 4.59 (d, 3H, $H_{ax}$, J=13.9 Hz), 4.55 (d, 3H, $H_a$, J=13.7 Hz), 4.49 (m, 6H, allyl), 4.16 (m, 12H, O—$CH_2$—$CH_2$—O), 3.74 (s, 9H, O—$CH_3$), 3.40 (d, 3H, $H_{eq}$, J=13.5 Hz), 3.37 (d, 3H, $H_{eq}$, J=13.4 Hz). $^{13}$C NMR ($CDCl_3$) $\delta$=149.95, 149.21, 147.53, 146.96, 134.53, 134.36, 134.02, 132.51, 131.91, 122.35, 120.94, 117.17, 116.89, 114.47, 70.27, 69.83, 69.58, 56.48, 36.43. HRMS calcd for $C_{60}H_{60}O_{12}$ (M+MeCN+Na$^+$) 1036.4248. found 1036.4261.

Tri-OH Cryptophane

Tri-allyl cryptophane (303 mg, 0.31 mmol), triphenylphosphine (135 mg, 0.51 mmol), palladium acetate (7.7 mg, 0.03 mmol), diethylamine (1.5 g, 20.5 mmol), THF (4.8 mL), and water (0.95 mL) were added to a screw-capped high-pressure tube. The tube was purged with nitrogen, sealed, and placed in an 80° C. oil bath with magnetic stirring for 4 h. After cooling to rt, the solvent was removed by evaporation under reduced pressure. The crude material was dissolved in $CH_2Cl_2$ (100 mL), washed twice with 1 M HCl (50 mL) and once with saturated NaCl (50 mL). The crude material was then adsorbed onto silica gel and purified by column chromatography ($CH_2Cl_2 \rightarrow 90:20$ $CH_2Cl_2$:acetone) to yield 220 mg (84% yield) of Tri-OH Cryptophane as a white solid. $^1$H NMR (DMSO-$d_6$) $\delta$=8.50 (s, 3H, Ar—OH), 6.83 (s, 3H, aryl), 6.77 (s, 3H, aryl), 6.60 (s, 3H, aryl), 6.53 (s, 3H, aryl), 4.50 (d, 3H, $H_{ax}$, J=13 Hz) 4.40 (d, 3H, $H_a$, J=13 Hz), 4.20-4.00 (m, 12H, O—$CH_2$—$CH_2$—O), 3.73 (s, 9H, Ar—$OCH_3$), 3.31 (d, 3H, $H_{eq}$, J=14 Hz), 3.15 (d, 3H, $H_{eq}$, J=14 Hz). $^{13}$C NMR (DMSO-$d_6$) $\delta$=148.91, 146.59, 145.81, 144.29, 133.79, 133.33, 131.15, 129.58, 120.62, 120.10, 117.45, 114.22, 68.50, 55.72, 35.03. HRMS calcd for $C_{51}H_{48}O_{12}$ (M+Na$^+$) 875.3043. found 875.3053.

Tri-EtOAc Cryptophane

Tri-OH cryptophane (189 mg, 0.22 mmol) and cesium carbonate (0.43 g, 1.3 mmol) were added to an oven-dried flask with stir bar and purged with nitrogen gas. Dry DMF (5 mL) was added by syringe and the mixture was allowed to stir for 30 min at rt. Ethyl bromoacetate (0.22 g, 1.33 mmol) was then added and the reaction was placed in a 60° C. oil bath with stirring overnight. The DMF was removed by evaporation under reduced pressure. The crude reaction mixture dissolved in $CH_2Cl_2$ (50 mL), washed with saturated NaCl (50 mL), dried over $Na_2SO_4$, and evaporated under reduced pressure. The crude material was then pumped under high vacuum to remove any residual DMF and purified by column chromatography ($CH_2Cl_2 \rightarrow 90:20$ $CH_2Cl_2$:diethyl ether) to yield 0.194 g (79% yield) of Tri-EtOAc Cryptophane as a white solid. $^1$H NMR ($CDCl_3$) $\delta$=6.76 (s, 3H, aryl), 6.75 (s, 3H, aryl), 6.71 (s, 3H, aryl), 6.69 (s, 3H, aryl), 4.58 (d, 3H, $H_{ax}$, J=14 Hz), 4.55 (d, 3H, Ar—O—$CH_2$—$CO_2$, J=16 Hz), 4.54 (d, 3H, $H_{ax}$, J=14 Hz), 4.50 (d, 3H, Ar—O—$CH_2$—$CO_2$, J=16 Hz), 4.32-4.19 (m, 18H, O—$CH_2$—$CH_2$—O, $CO_2$—$CH_2$—$CH_3$), 3.76 3.67 (s, 9H, Ar—$OCH_3$), 3.40 (d, 3H, $H_{eq}$, J=14 Hz) 3.38 (d, 3H, $H_{eq}$, J=14 Hz), 1.35 (t, 9H, $CH_2$—$CH_3$, J=7 Hz) $^{13}$C NMR ($CDCl_3$) $\delta$=168.74, 149.73, 148.02, 147.73, 146.79, 134.02, 133.95, 133.73, 131.79, 121.88, 120.62, 118.18, 114.71, 69.56, 69.24, 67.20, 61.20, 56.21, 36.20, 36.11, 14.34. HRMS calculated for $C_{63}H_{66}O_{18}$ (M+Na$^+$) 1133.4147. found 1133.4134.

Tri-Acetic Acid Cryptophane (TAAC)

Tri-EtOAc cryptophane (194 mg, 0.17 mmol), 2 M KOH (7.35 mL), and THF (8.75 mL) were added to a screw-capped high-pressure tube. The tube was purged with nitrogen, sealed, and placed in a 70° C. oil bath with magnetic stirring overnight. The THF was then removed by evaporation under reduced pressure. The aqueous solution was transferred to a centrifuge tube, acidified with 12 M HCl and centrifuged. The solid pellet was redissolved in 1 M NaOH, acidified with 12 M HCl and centrifuged. The solid pellet was then dispersed in deionized water, centrifuged, and the water decanted. After lyophilization of the resulting pellet, 0.1559 g of tri-acid cryptophane was obtained in 87% yield. $^1$H NMR (DMSO-$d_6$) $\delta$=6.85 (s, 3H, aryl), 6.83 (s, 3H, aryl), 6.82 (s, 3H, aryl), 6.77 (s, 3H, aryl), 4.54 (s, 6H, Ar—O—$CH_2$—$CO_2$), 4.48 (d, 6H, $H_{ax}$, J=13 Hz), 4.06-4.25 (m, 12H, O—$CH_2$—$CH_2$—O), 3.67 (s, 9H, Ar—$OCH_3$), 3.31 (d, 3H, $H_{eq}$, J=13 Hz), 3.28 (d, 3H, $H_{eq}$, J=13 Hz). $^{13}$C NMR ($d_6$-DMSO) $\delta$=170.16, 148.75, 147.173, 145.60, 133.55, 133.45, 132.42, 131.69, 120.41, 118.95, 115.86, 114.96, 68.64, 68.17, 65.49, 55.87, 34.88. HRMS calcd for $C_{57}H_{54}O_{18}$ (M+Na$^+$) 1049.3208. found 1049.3211.

Isothermal Titration Calorimetry (ITC)

ITC samples were prepared and experiments were performed using a MicroCal VP-ITC titration microcalorimeter (Northampton, Mass.) at 293 K. Standard protocols and data analysis were used. Control enthalpograms are given in the appended figures.

Steady-State Fluorescence

Steady-state fluorescence spectra were acquired using a Varian Cary Eclipse fluorimeter equipped with a Peltier multicell holder for temperature control. Concentration measurements necessary for fluorescence work were obtained using an Agilent 8453 UV-Vis spectrophotometer. Xenon binding determination by fluorescence quenching was performed. The quantum yield of tri-acid cryptophane was measured relative to tryptophan.

Aqueous NMR Spectroscopy 180 mM solutions were made by deprotonation of 0.011 mmol tricarboxylate cryptophane and tritriazole propionate cryptophane using sodium deuteroxide 40 wt. % in $D_2O$ and subsequent dissolution in 600 μL 10% $D_2O/H_2O$. These samples were transferred to 5 mm controlled atmosphere valve sample tubes (New Era Spectroscopy) to allow for degassed- and xenon-saturated $^1H$ NMR spectroscopy.

Time-Resolved Fluorescence

Time-resolved fluorescence measurements were performed at 293 K using the time-correlated single photon counting (TCSPC) method. The TCSPC system consisted of the third harmonic of a Ti:sapphire femtosecond laser (Coherent Chameleon) generating 80 MHz output pulses at 275 nm, a subtractive double monochromator with a MCP-PMT (Hamamatsu R2809U) and a TCSPC board (Becker & Hickl, SPC-730). Emission at 310 nm was monitored. Data analysis was done using the FLUOFIT software (Picoquant GmbH). Fluorescence decays were deconvolved with an instrument response function of 35 ps.

Example 1

Synthesis of Triacetic Acid Cryptophane (TAAC)

Tricarboxylate Cryptophane (1) was synthesized (FIG. 1) by a modification of the synthesis of monoallyl-cryptophane by Darzac et al. {Darzac et al., Chem Commun (Camb). 2002 Jan. 7; (1):48-9. "Cryptophanols, new versatile compounds for the synthesis of functionalized cryptophanes and polycryptophanes".} Cyclotriveratrylene 3 in DMF was deprotonated with cesium carbonate and reacted with 4.5 equiv 2-[3-allyloxy-4-(2-iodo-ethoxy)-benzyloxy]-tetrahydropyran 4 at 55° C. in 60% yield to obtain 5.

In 50:50 chloroform:formic acid, the cyclization of 5 proved extremely slow at 55° C. and higher temperatures were necessary to push the reaction past a partially cyclized intermediate. It is hypothesized that the three allyl groups provided enough steric hinderance to allow the observation of this intermediate. An optimum reaction time of 9 h at reflux was to found (Table 1) to give triallyl-cryptophane 6 in 40% yield, compared to 2.5 h at 55° C. for monoallyl-cryptophane. {Darzac, 2004 #18} Use of a higher boiling solvent system, 50:50 1,2-dichloroethane:formic acid, led to decomposition of 5. The cyclized product 6 was isolated as the anti isomer, as confirmed by X-ray crystallography of the empty crown-saddle (CS) isomer (vide infra).

TABLE 1

Reaction times and yields for formation of tri-allyl cryptophane

| Reaction Condition | Temp (° C.) | Time (h) | Yield |
|---|---|---|---|
| HCOOH, CHCl$_3$ | 55 | 2.5 | 0% |
| HCOOH, CHCl$_3$ | reflux | 3 | 17% |

TABLE 1-continued

Reaction times and yields for formation of tri-allyl cryptophane

| Reaction Condition | Temp (° C.) | Time (h) | Yield |
|---|---|---|---|
| HCOOH, CHCl$_3$ | reflux | 6 | 32% |
| HCOOH, CHCl$_3$ | reflux | 9 | 40% |
| HCOOH, CHCl$_3$ | reflux | 22 | 25% |
| HCOOH, Cl(CH$_2$)$_2$Cl | reflux | 1 | decomp |

Deprotection of 6 to the triphenol-cryptophane 7 was accomplished in 84% yield by palladium catalysis using known procedures. {Brotin, 2005 #20} The triphenol 7 was then triply alkylated using ethylbromoacetate and cesium carbonate in DMF to yield triester-cryptophane 8 in 79% yield. Saponification of 8 in tetrahydrofuran using potassium hydroxide yielded triacid-cryptophane 1 in 87% yield. The conversion of starting 3,4-dihydroxybenzaldehyde to 1 occurred in 13 steps in 1.7% overall yield.

Example 2

Binding of Xenon by Tricarboxylate Cryptophane

Figure 2:
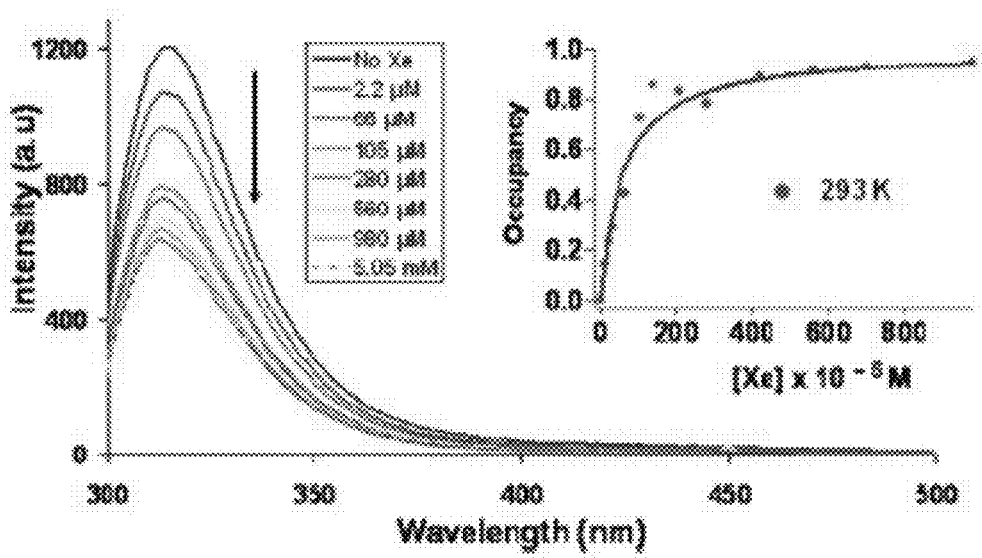
FIG. 2 shows fluorescence quenching of tritriazole propionate cryptophane (TTPC) (15 μM) by Xe in 1 mM, pH 7.2 phosphate buffer, 293 K. Inset: Curve fits for a single-site binding model.
Figure 3:
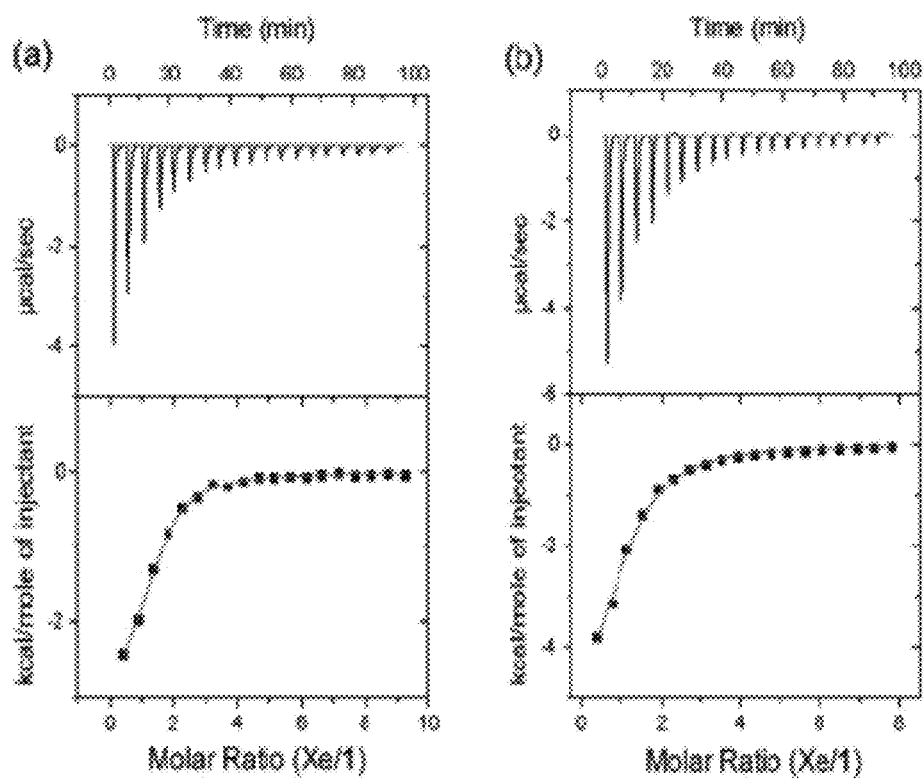
FIG. 3 shows enthalpograms of (a) tri-triazole propionate cryptophane (TTPC) (88 μM) in phosphate buffer at 310 K titrated with saturated aqueous xenon (3.3 mM); and (b) tri-triazole propionate cryptophane (TTPC) (112 μM) in human plasma at 310 K titrated with xenon-saturated plasma (4.0 mM)
Figure 4:
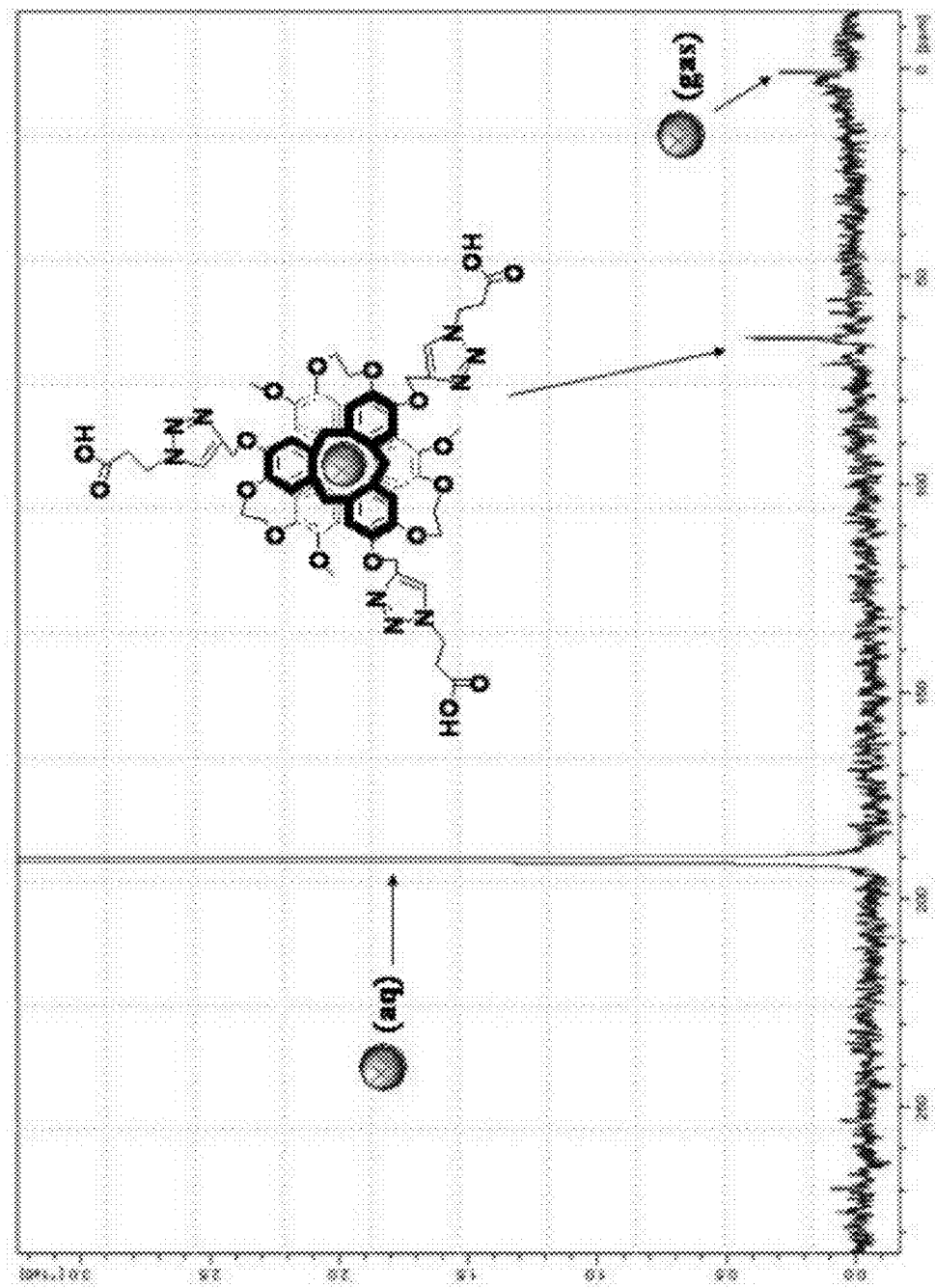
FIG. 4 shows hyperpolarized $^{129}$Xe spectrum of 60 μM tritriazole propionate cryptophane (TTPC) in 1 mM pH 7.2 phosphate buffer.
Figure 5:
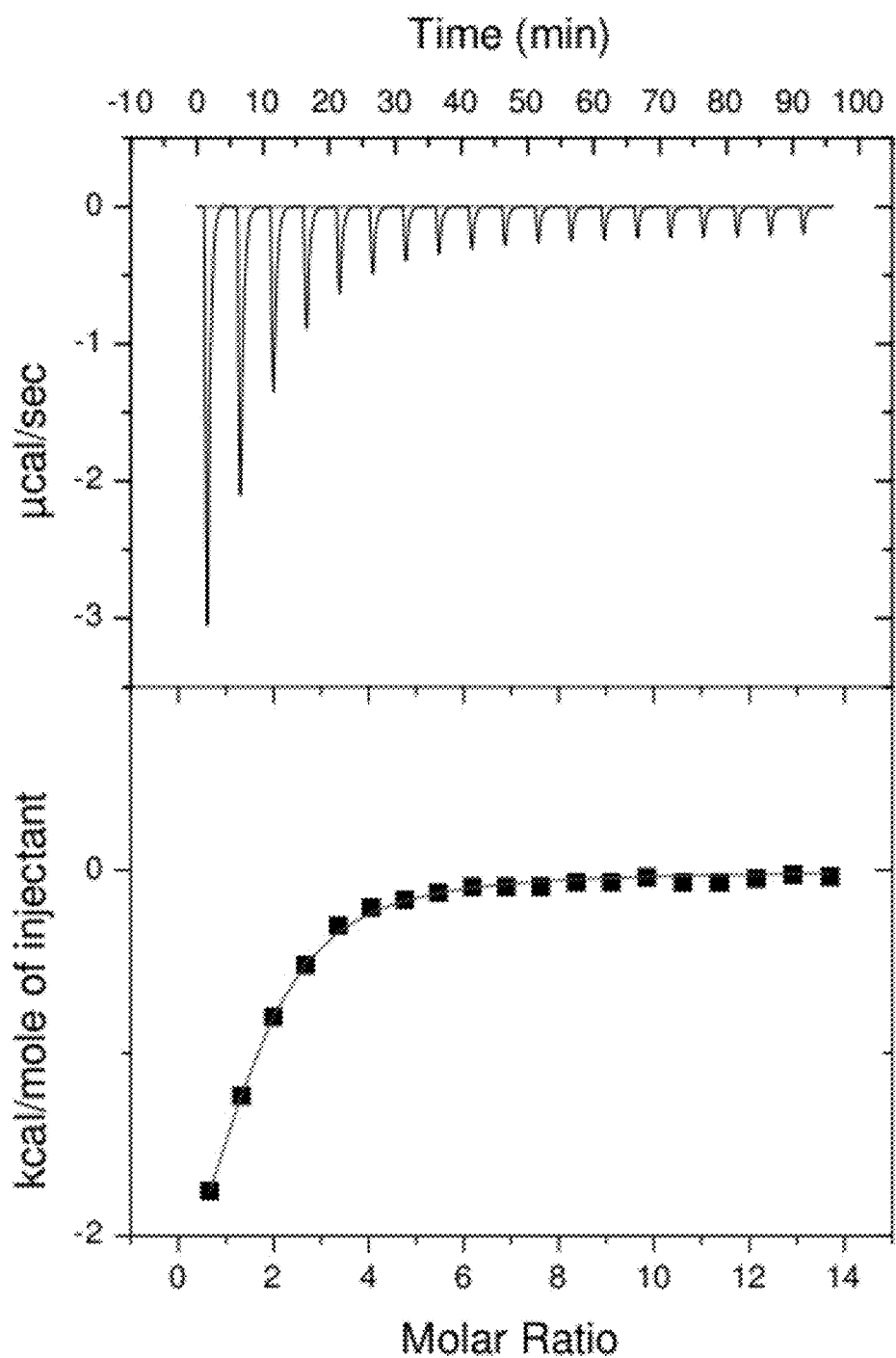
FIG. 5 shows enthalpograms of tri-triazole propionate cryptophane (80 μM) in 20 mM, pH 7.5 phosphate buffer at 293 K titrated with saturated aqueous xenon (5.05 mM)
Figure 6:
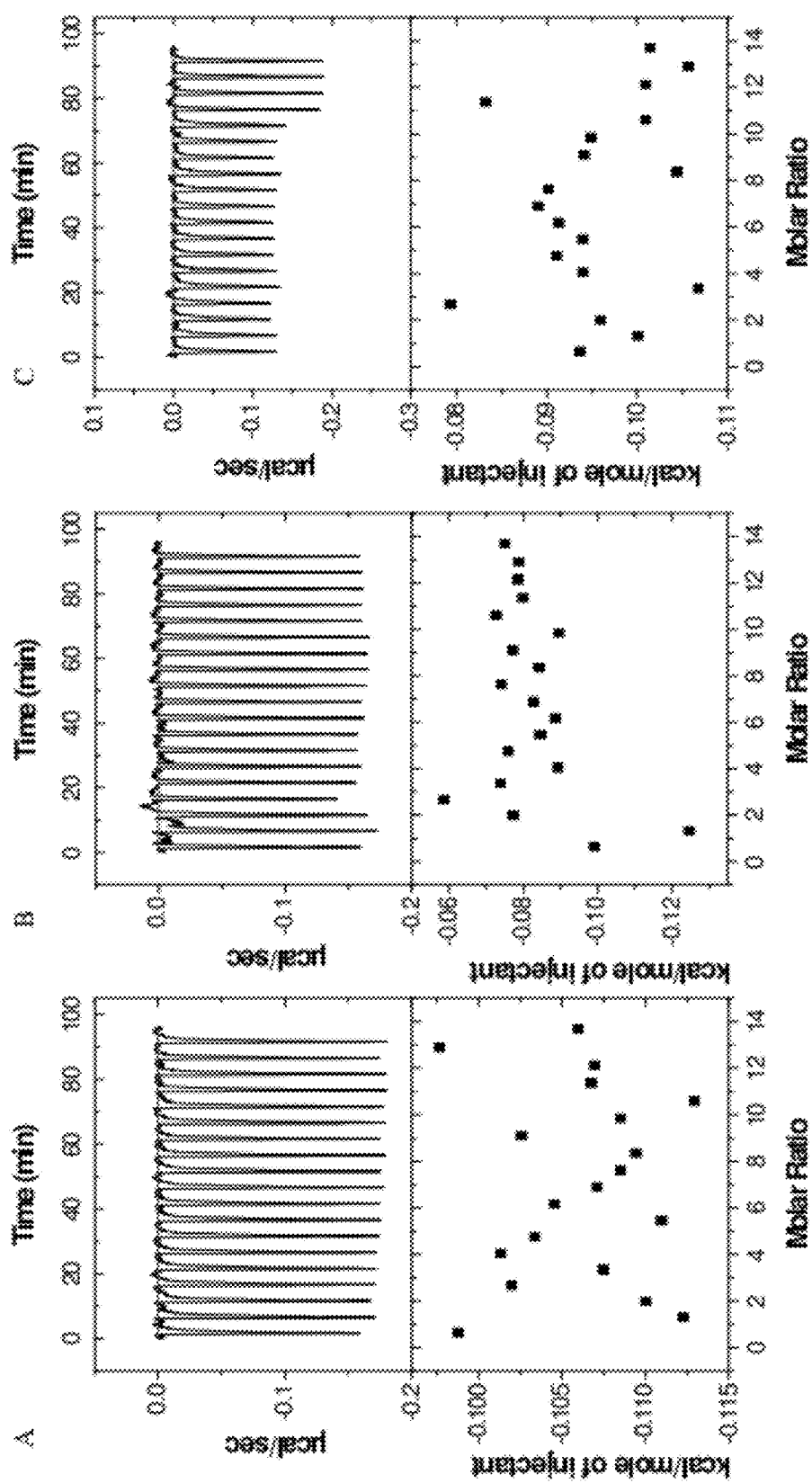
FIG. 6 shows buffer controls at 293 K: a) Water titrated into 20 mM phosphate buffer b) Water titrated into a solution of tri-triazole propionate cryptophane (TTPC) in 20 mM phosphate buffer, [TTPC]=80 μM c) Xenon-saturated water titrated into 20 mM phosphate buffer, MeI=5.05 mM.
Figure 7:
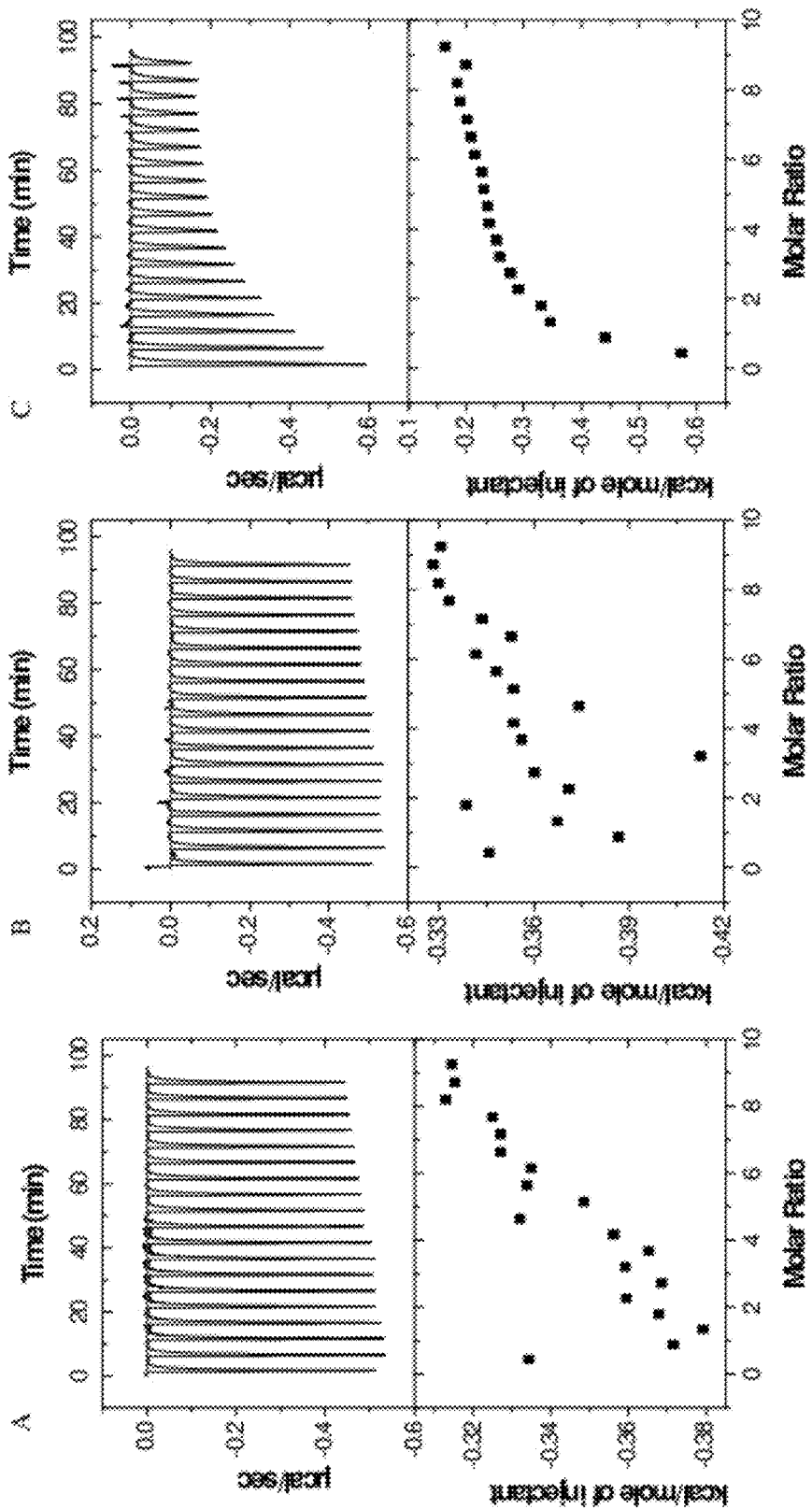
FIG. 7 shows buffer controls at 310 K: a) Water titrated into 20 mM phosphate buffer; b) Water titrated into a solution of tri-triazole propionate cryptophane (TTPC) in 20 mM phosphate buffer, [TTPC]=88 μM; c) Xenon-saturated water titrated into 20 mM phosphate buffer, [Xe]=3.3 mM.
Figure 8:
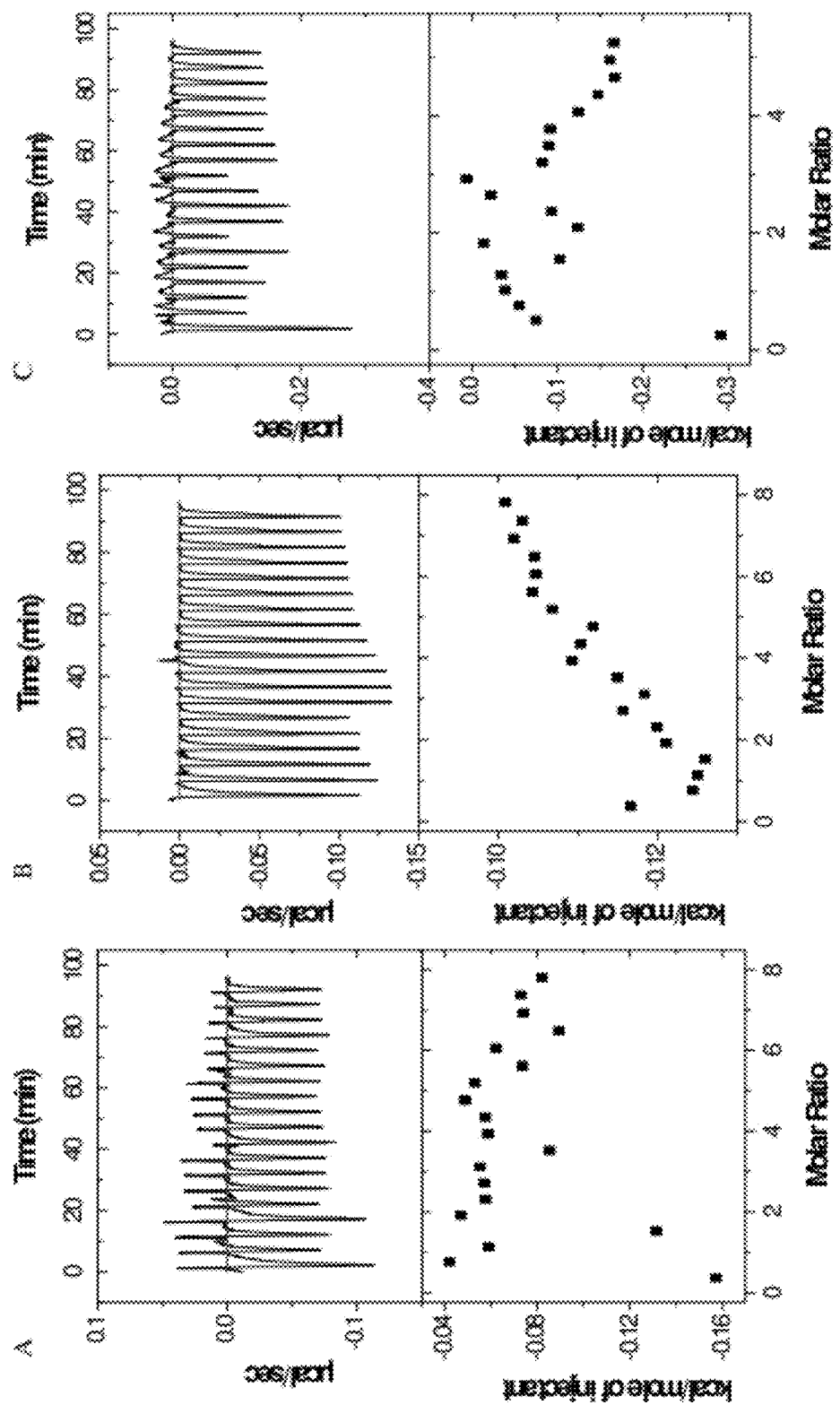
FIG. 8 shows plasma controls at 310 K: a) plasma titrated into plasma; b) tri-triazole propionate cryptophane (TTPC) in plasma titrated into plasma, [TTPC]=112 μM; c) xenon-saturated plasma titrated into plasma, [Xe]=4 mM.

The xenon affinity of tricarboxylate cryptophane was studied by fluorescence quenching (FIG. 2) and isothermal titration calorimetry (ITC) (FIG. 3). An extinction coefficient of 12,040 $M^{-1}$ $cm^{-1}$ at 280 nm was determined for TAAC, varying only slightly from the previously determined value of $\epsilon_{280}$=12,400 $M^{-1}$ $cm^{-1}$ for tri-triazole propionate cryptophane (TTPC). As in a previous fluorescence quenching study with TTPC, temperature-equilibrated solutions of xenon-saturated water were added sequentially by syringe to a septum-sealed fluorescence cuvette and fluorescence intensity measurements were taken. An association constant of 33,000±2000 $M^{-1}$ at 293 K was obtained for TAAC to by this method. No measurable change in the absorption spectra of either triacetic acid cryptophane (TAAC) or tri-triazole propionate cryptophane (TTPC) was observed upon xenon saturation.

In order to confirm the association constants obtained by fluorescence quenching, ITC experiments were performed. ITC was used previously to determine the xenon binding affinity for TTPC and more recently for a water-soluble cucurbit[6]uril derivative. ITC measurements were performed at 293 K on 0.77 mM TAAC in 20 mM, pH 7.5 phosphate buffer (FIG. 2), which gave a ΔH of −4.3±0.7 kcal*mol$^{-1}$. From these data, ΔS of 5.9 cal*mol$^{-1}$*K$^{-1}$ and ΔG of −6.09 kcal*mol$^{-1}$ were calculated. The xenon association constant, $K_A$=33,000±3000 $M^{-1}$, determined for TAAC was significantly higher than that determined previously for TTPC, $K_A$=17,000±2000 $M^{-1}$. Thermodynamic parameters for TAAC and TTPC are compared in Table 2.

TABLE 2

Thermodynamic Binding Parameters of Xe@1 Obtained by ITC at 293 K

| Cryptophane | $K_A$ ($M^{-1} \times 10^4$) | ΔG (kcal mol$^{-1}$) | ΔH (kcal mol$^{-1}$) | TΔS (kcal mol$^{-1}$) |
|---|---|---|---|---|
| TAAC | 3.33 ± 0.28 | −6.06 | −4.34 ± 0.66 | 1.72 |
| TTPC | 1.70 | −5.69 | −3.14 | 2.55 |

Example 3

Fluorescence Spectroscopy

The room-temperature fluorescence spectra of TAAC and TTPC consisted of a broad band with a maximum at 313 nm in phosphate buffer, similar to the six 1,2-dialkoxybenzenes that the form the cryptophane. TAAC exhibited a higher quantum yield than TPCC ($\Phi_f$=0.06 vs. 0.01 at 293 K) and a greater degree of quenching upon xenon saturation ($F_o$/F=6 vs. 2). The emission of both molecules was partially quenched by oxygen, implying weak oxygen binding. Because the only chemical difference between TAAC and TTPC is the nature of the pendant solubilizing groups, the lower quantum yield of TTPC could be explained by excited-state quenching by the three triazole rings appended to its cryptophane core. The quantum yield of TAAC is also temperature dependent, with a linear decrease of 0.0007/K between 283 and 313 K. This temperature dependence is attributed to the increase in molecular motions and accessibility of different cage conformations as the thermal energy of the cryptophane system is increased.

Figures 13, 14:
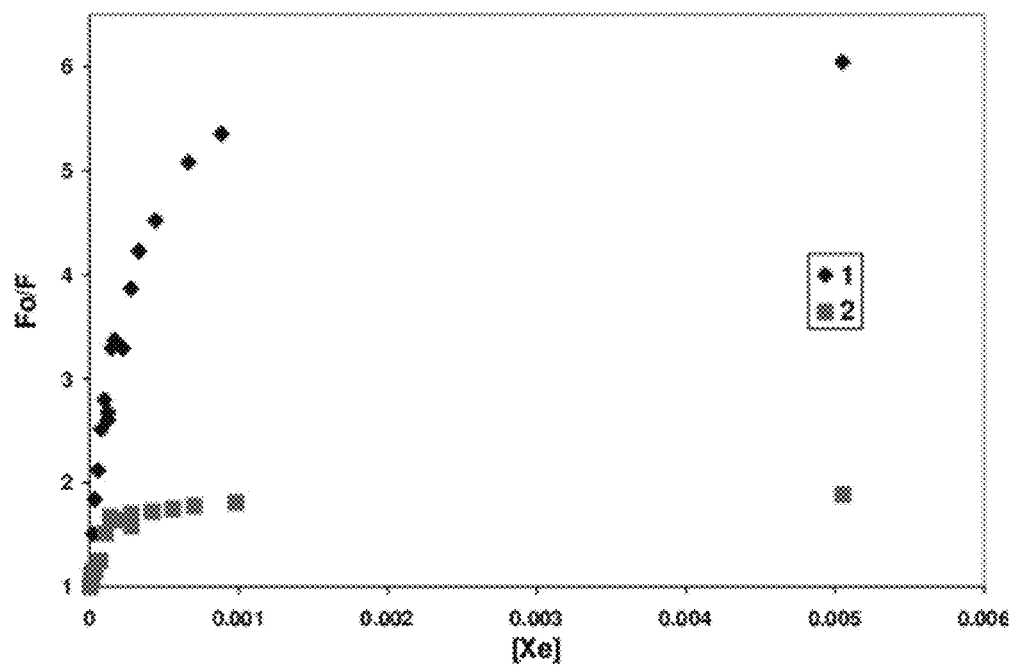
FIG. 13 shows Stern-Volmer plots of fluorescence quenching of TAAC and TTPC by xenon. Diamonds are TAAC, squares are TTPC.
FIG. 14 shows initial slopes of Stern-Volmer plots of TAAC and TTPC. Diamonds are TAAC and squares are TTPC.

The Stern-Volmer plots for TAAC and TTPC indicate the amount of fluorescence quenching ($F_o$/F) observed at various xenon concentrations (FIG. 13). While a linear correlation is observed at low xenon concentrations, a horizontal deviation from linearity is observed at higher xenon concentrations approaching maxima at $F_o$/F=6 for TAAC and $F_o$/F=2 for TTPC at xenon saturation. Fits to the initial linear sections of the plots give slopes of 19,300 $M^{-1}$ and 4,700 $M^{-1}$, respectively, for encapsulated xenon quenching (FIG. 14). Horizontal deviations in Stern-Volmer plots are normally observed when there is hindered access to a particular population of fluorophores in a sample While it may be conceivable that a co-encapsulated water molecule could prevent xenon from contacting one of the six 1,2-dialkoxybenzene chromophores of the cryptophane cores of TAAC and TTPC, aqueous NMR measurements found no evidence of encapsulated water, even under degassed conditions (vide infra).

Time-correlated single-photon counting (TCSPC) measurements of the fluorescence lifetimes of TAAC and TTPC were undertaken in an effort to understand the nature of the xenon quenching and the horizontal deviation from linearity in the steady-state Stern-Volmer plots The low quantum yield and short lifetime of TTPC allowed only mono-exponential tailfits to be obtained, giving lifetimes of ~300 ps without encapsulated xenon and ~200 ps when saturated with xenon.

Figure 15:
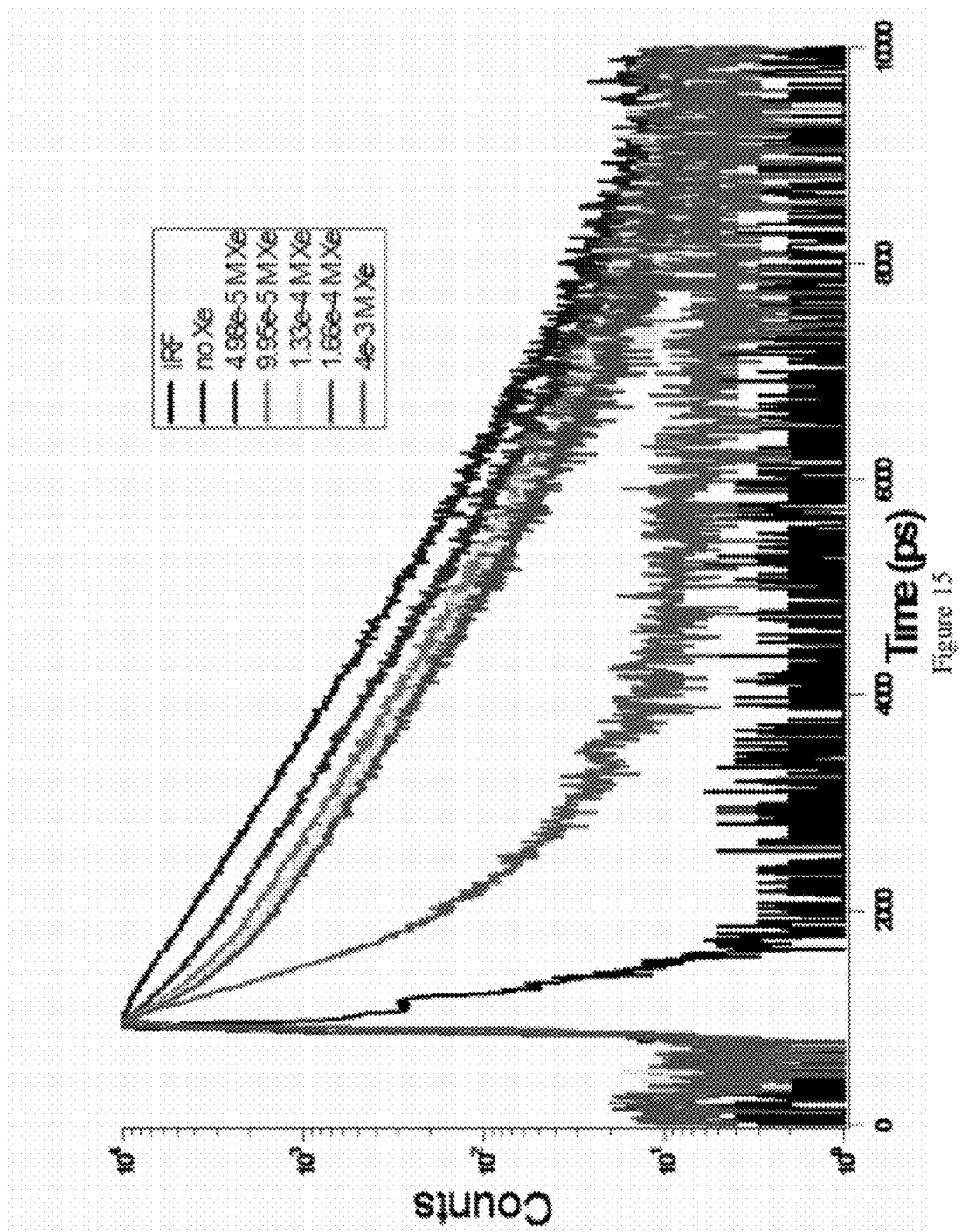
FIG. 15 shows fluorescence decays of TAAC with addition of increasing amounts of xenon.
Figure 19:
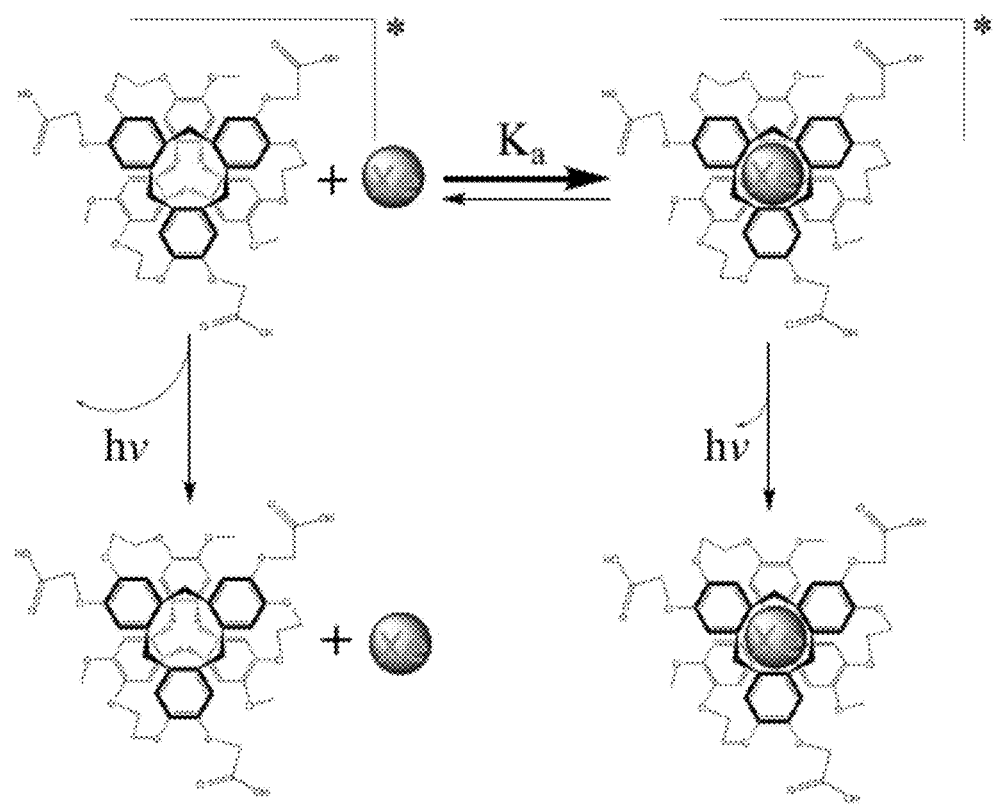
FIG. 19 shows the proposed model of fluorescence quenching of triacetic acid-functionalized cyptophane (TAAC) by encapsulated xenon.

The higher quantum yield of TAAC allowed for decay fits deconvolved from the TCSPC instrument response function. Rigorously purified TAAC in aqueous solution exhibited a double exponential decay (FIG. 15), which was fitted to two exponentials with lifetimes of 1.1 ns (91% of total intensity) and 0.7 ns (9% of total intensity). The smaller amplitude, shorter-lived component is consistent with the presence of another conformer in solution. As a comparison, the lifetime of 1,2-dimethoxybenzene is monoexponential with a lifetime of 1.4 ns. Upon xenon encapsulation, a very short-lived component with lifetime of 0.16 ns replaced the 1.1 ns lifetime. This new lifetime is not expected to be a result of collisional quenching between non-encapsulated xenon and the excited state of TAAC as the diffusion rate of xenon in water (2.2±0.4*$10^{-5}$ $cm^2$ $s^{-1}$) and the short timescale of the fluorescence decays give a root-mean-square distance of 22 Å that aqueous xenon must travel to quench the $S_1$ state. At the highest concentrations (~15 µM 1 and 5 mM Xe) investigated in these fluorescence experiments, there was an average spacing of 70 Å between xenon atoms. Also, given the long residence time of xenon in an aqueous cryptophane cage (30 to ms), xenon exchanging in and out of the cage is not likely a factor in these measurements. From the fluorescence measurements of TAAC with no encapsulated xenon, a natural lifetime ($\tau_n$) of 19 ns, its reciprocal emissive rate ($\Gamma$) of 5.3*$10^7$ $s^{-1}$, and a nonradiative decay rate ($k_{nr}$) of 8.56*$10^8$ $s^{-1}$ were obtained. An apparent first-order quenching rate constant for xenon quenching the fluorescence of TCC, $k_q$=5.34*$10^9$ $s^{-1}$, was then computed from the lifetime of TAAC saturated with xenon. Based on the observed steady-state quenching and quantum yield of TCC, a $\Phi_f$ of 0.01 has been calculated for the species Xe@1. These observations are summarized in a modified static quenching scheme (FIG. 19) in which the effect of adding xenon to a solution of TAAC converts the population from the more emissive "empty" TAAC* excited state to a population of less emissive Xe@1*, as governed by the binding affinity of xenon by TCC.

Example 4

Acid-Base Titration

Acid-base titrations of TAAC and TTPC were performed in order to understand the solubility requirements and anion stabilities of the molecules. TAAC exhibited a $pK_a$ of 4.1, compared to the $pK_a$ of 3.23 for the analagous 2-(2-methoxyphenoxy)acetic acid. Previous studies of sterically congested acetic acid derivatives have shown $pK_a$ differences of this magnitude. Steric congestion near the carboxylic acid group decreases acidity by preventing efficient solvation of the carboxylate anion. For compound TAAC, this is due to the large nonpolar surface of the cryptophane interfering with the solvation of the carboxylate base. Each acid group attached to TAAC can be approximated as being an acetic acid attached to a ~1 nm diameter nonpolar sphere. Water molecules surrounding the nonpolar cryptophane surface must be ordered, a consequence of the hydrophobic effect. Carboxylate solvation must directly compete with this ordered solvation sphere necessary for the cryptophane core. In addition, based on visual observations of precipitation during the titrations, it was found that TAAC required all three acids to be deprotonated for aqueous solubility while TTPC required only two deprotonations for solubility to 200 µM.

The carboxylate groups of TTPC are ~5 Å farther from the cryptophane core than in TAAC and more easily stabilized through solvation. Titration of TTPC under the same conditions as TAAC yielded a $pK_a$ of 5.3. The $pK_a$ difference between TTPC and the analogous propanoic acid ($pK_a$=4.87) is less than one-half of a $pK_a$ unit, indicative that the carboxylates on TTPC experience less effect from the bulk of the nonpolar cryptophane. Propanoic acid is relevant for comparison to TTPC as the triazoles on TTPC are greater than two methylenes from the acid groups and not expected to contribute electrostatically to their acidity. However, the dipole moments and hydrogen-bond accepting abilities of the three triazoles appended to TTPC are expected to aid solubility.

Example 5

Aqueous NMR Spectroscopy

In order to bind xenon, the cryptophanes in this study must exist in a $C_3$-symmetric crown-crown (CC) conformation, in which both cyclotriveratrylene (CTV) units adopt a concave form to create a molecular cavity. However, water-soluble cryptophanes are capable of existing in multiple conformations in aqueous solution. Specifically, a crown-saddle (CS)

conformation, in which one of the two CTV units of the cryptophane is in an asymmetric "saddle" conformer was previously proposed. The CTV unit possessing the saddle conformer has been proposed to fill the cavity of the cryptophane, preventing xenon binding.

Figure 16:
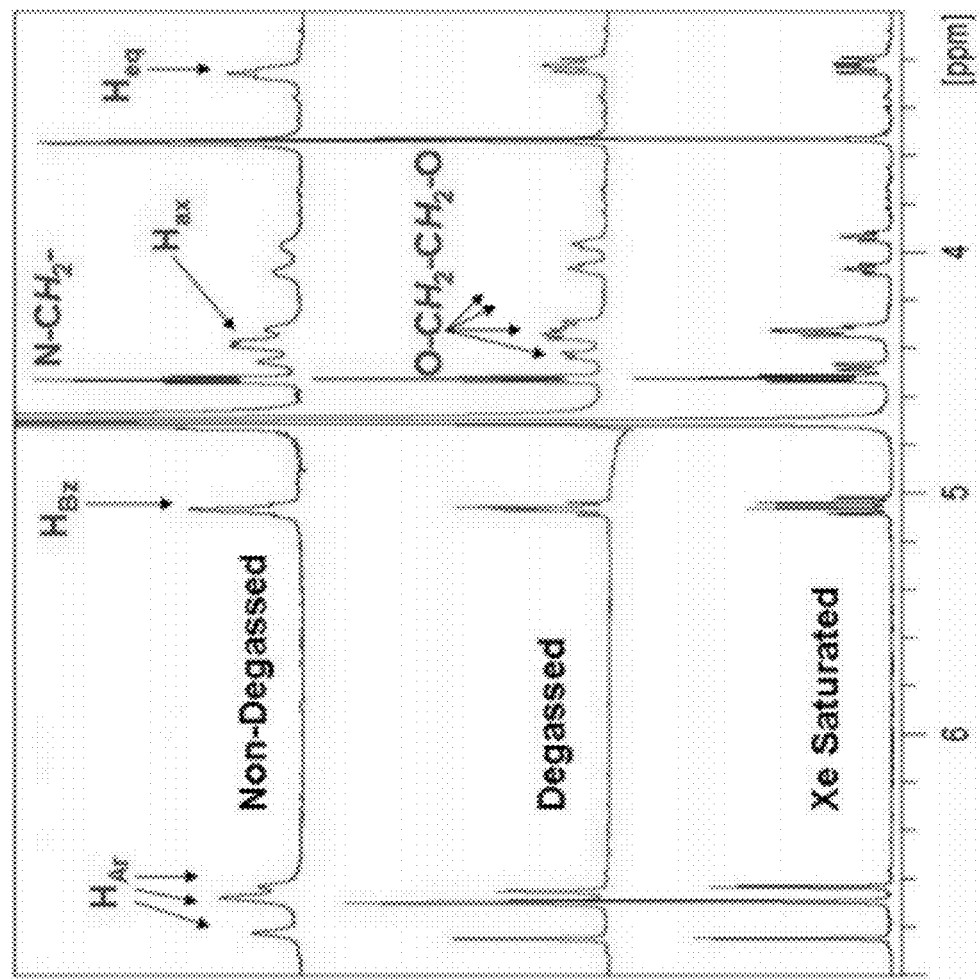
FIG. 16 shows a 600 MHz $^1$H NMR spectrum of TTPC in 10% $D_2O$.
Figure 16:
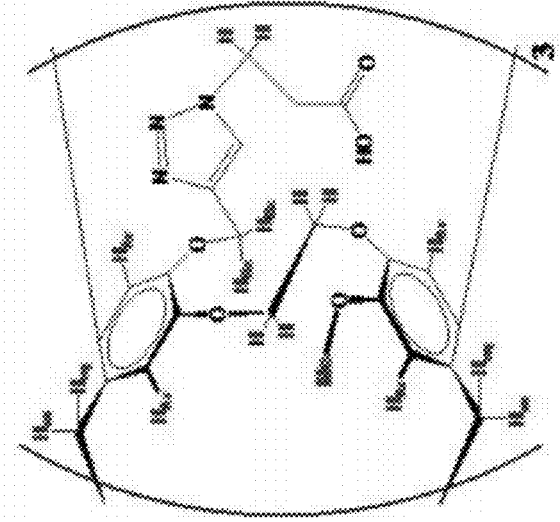

It should be noted in TTPC (FIG. 16) that the protons furthest from the cryptophane core exhibit sharp linewidths (N—$CH_2$ protons FWHM=3 Hz for all three conditions) that are not affected by the nature of the various gaseous guest molecules. Degassing the solution with several cycles of pumping under static vacuum significantly sharpened the aromatic and ethylene linker resonances. Because the cryptophane core is chiral (a mixture of $M_o$ and $P_o$ enantiomers), the protons on the methylene connecting the cryptophane ("$H_{Bz}$" in FIG. 16) to the triazole are diastereotopic, their resonances separated by 0.04 ppm and geminally splitting each other by 12 Hz upon xenon saturation. Most notably, however, no population of conformers other than the canonical CC form was detected for TTPC.

Figure 17:
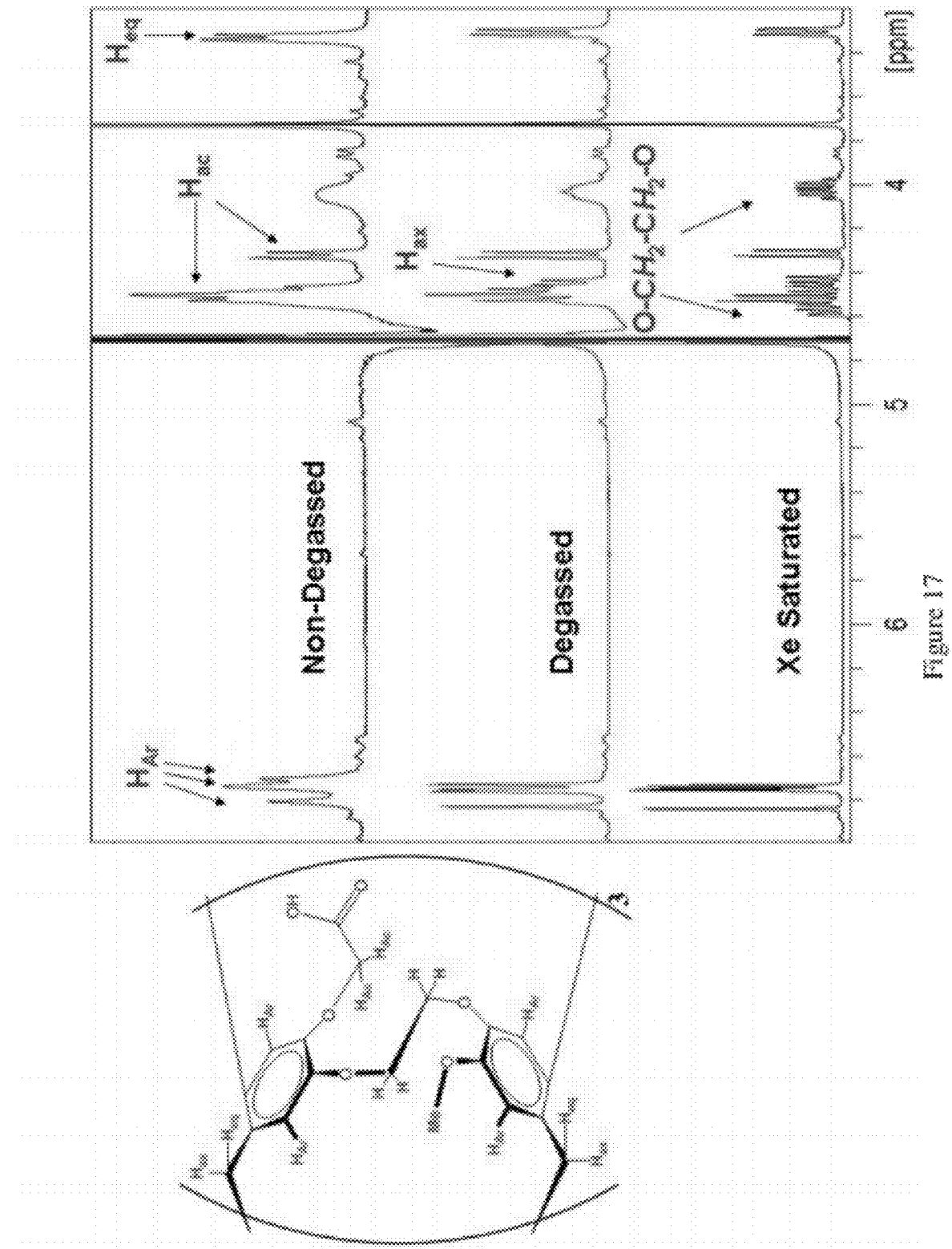
FIG. 17 shows a 600 MHz $^1$H NMR spectrum of TAAC in 10% $D_2O$.

The degassed aqueous NMR spectrum of TAAC indicated less than 5%, by NMR integration, population of a second species that is consistent with the CS conformer. In addition to the aromatic peaks that are a result of the $C_1$ symmetry of the CS conformer, the bridging methylene group peaks at 0.0 and 2.0 ppm that correspond to the $CH_2$ protons pointing into the cavity These peaks are not impurities as the $^1$H NMR of 1 in $d_6$-DMSO (molecular charge=0), shows only CC conformer without the need for degassing or xenon saturation. Another striking feature of TAAC in aqueous solution is the magnitude of diastereotopic chemical shift difference evident in the protons on the methylenes connecting the cryptophane to the carboxyl groups ("$H_{Ac}$" in FIG. 17). These protons, as confirmed by to 2-D COSY, had resonances separated by 0.20 ppm with 15 Hz geminal splitting. This large difference in chemical shift between the two methylene protons is indicative of two very different chemical environments. When TAAC was dissolved in $d_6$-DMSO, the $H_{Ac}$ methylenes appeared as a singlet, with no apparent difference in their chemical environment. This dependence of chemical shift on the solvent and protonation state of TAAC indicates that the diastereotopism observed in aqueous solution is a result of the carboxylate anions being unable access many conformations that could produce magnetic equivalence of the protons. Adopting such conformations would lead to a loss in solvating water molecules and destabilize the anion. It is hypothesized that the CS conformer allows for more efficient solvation of the carboxylates, thermodynamically stabilizing this structure and allowing for its observation.

The NMR and titration data indicates that the CS conformer population of TAAC is caused by the three deprotonated carboxylates being poorly solvated due to their close proximity to the cryptophane core. This poor anion solvation destabilizes the CC conformer. The greater solvation gained through adoption of the CS conformer allows for the observation of both conformers in aqueous solution. The carboxylates of TTPC, being further from the cryptophane core, allow for a more efficient solvation of the anions, which eliminates the gain in solvation associated with adopting the CS conformation.

Example 6

CS Conformer Crystal Structure

Although not being unable to isolate the CS conformer of TAAC as a single species in aqueous solution growing a crystal triallyl-cryptophane in the CS conformer was possible. Single crystals of triallyl-cryptophane were obtained via dissolution in hot mesitylene, cooling to room temperature, and subjection to vapor diffusion conditions with n-pentane, triallyl-cryptophane crystallized in the monoclinic space group P2$_1$/n with two of the ally groups experiencing disorder in which there were two possible orientations of the groups. Some X-ray crystallographic details of triallyl-cryptophane are given in Table 4:

TABLE 4 triallyl-cryptophane crystal data

| Guest | Interior Volume | Guest Volume | Packing |
|---|---|---|---|
| Xe | 89 | 43 | 0.48 |

Figure 18:
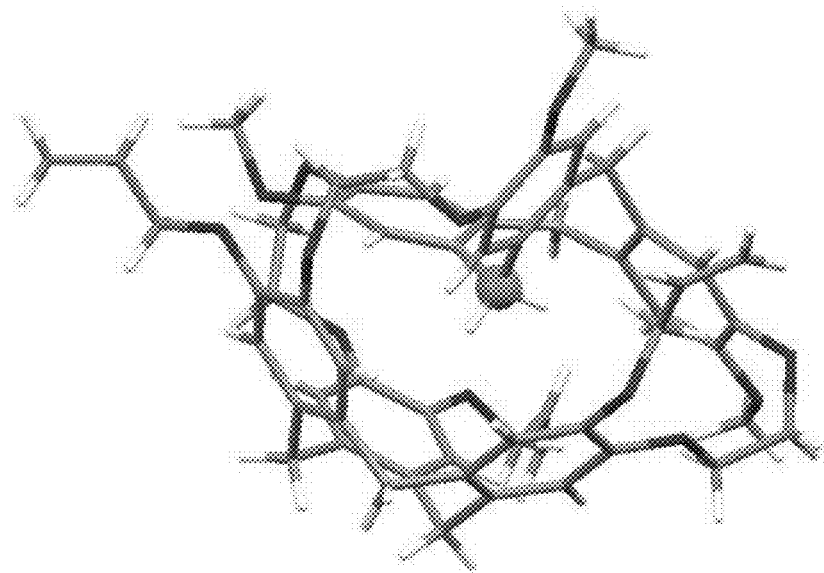
FIG. 18 shows crystal structure of crown-saddle (CS)-triallyl cryptophane (TAC). The bridging methylene group pointing into the collapsed cavity is shown as a green sphere.

The $C_1$ symmetric structure of the CS conformer of triallyl-cryptophane (CS-6) agrees well with the structure previously calculated and is shown in FIG. 18 with the inwardly pointed bridging methylene highlighted as a green sphere. The $CH_2$ protons of the bridging methylene group point into the cavity, analogous to the above discussed $^1$H NMR resonances of TAAC at 0.0 and 2.0 ppm in water, and have closest distances of 2.4 and 3.2 Å to the least-squared planes of the aromatic rings within the cavity of CS-6. It was impossible to find an internal void volume of CS-6 using Deep View/Swiss PDB Viewer as the internal cavity was too small to accommodate the 1.4 Å diameter probe. A CS conformer cryptophane possessing m-xylyl linkers between the CTV units has been studied by solution $^1$H NMR and single crystal X-ray diffraction To the inventors' knowledge, this is the first published crystal structure of the CS conformer of a cryptophane-A derivative.

Attempts to observe CS-triallyl-cryptophane by NMR spectroscopy through the degassing, heating, and cooling of a solution of triallyl-cryptophane in $d_{12}$ mesitylene were unsuccessful. Dissolution in $CDCl_3$ of crystals of CS-triallyl-cryptophane from the same preparation as the X-ray structural determination yielded only the CC conformer in solution. While it is expected that CS-triallyl-cryptophane is destabilized relative to the crown form of cyclotriveratrylene by 3-4 kcal mol$^{-1}$, it was concluded from these observations that crystal packing forces on triallyl-cryptophane in the absence of a guest promoted the adoption of the CS conformation.

Interestingly, the allyl-substituted CTV unit of CS-triallyl-cryptophane retained its crown conformation while the methoxy-substituted CTV unit (the second half of the same molecule), assumed the saddle conformation. In order to gain the most stability through solvation of its carboxylate anions, the acid-substituted CTV of compound TAAC undergoes inversion to the saddle isomer in order to maximize the solvent exposure of all three acid groups. However, in assuming the less sterically bulky CS conformation, the carboxylates of TAAC are better solvated regardless of conformation of the carboxylate-bearing CTV unit.

Example 7

Entropy Promotes Xenon Binding to Cryptophane in Water and Human to Plasma

An investigation as to whether xenon binds cryptophane in biological media, was sought as xenon is an anesthetic and associates weakly with many proteins, as well as lipids. TTPC (FIG. 1) was synthesized and determined by two complementary techniques to have unprecedented affinity for xenon, in water and human plasma.

Previous determinations of aqueous xenon binding constants for small molecules have relied on NMR measurements either through the analysis of $^1$H chemical shifts in the presence of xenon or on the direct integration of free and bound $^{129}$Xe resonances. The binding affinities for xenon of α-cyclodextrin, cucurbitril, and Huber's series of water-soluble hexa-acid cryptophanes were measured in this manner. In this Example, a more sensitive fluorescence quenching and isothermal calorimetry (ITC) methods for studying xenon binding to TTPC, that involved titration of aqueous xenon solutions.

A facile synthesis was developed for water-soluble cryptophane based on the copper (I)-mediated [3+2]azide-alkyne Huisgen cycloaddition. The ten-step synthesis, shown in FIG. 1, yielded triacid-functionalized cryptophane (TTPC) in 4% overall yield. TTPC (2 mM) was readily dissolved in aqueous base and remained soluble in 100 mM NaCl to pH ~5.5. A solution of TTPC (60 μM) in 1 mM, pH 7.2 phosphate buffer had a hyperpolarized $^{129}$Xe NMR chemical shift of 64.6 ppm. $^1$H NMR measurements of TTPC in D$_2$O showed only the crown-crown structural isomer at temperatures as high as 333 K. No evidence for a crown-saddle isomer was detected, as mentioned in the examples hereinabove.

TTPC exhibited similar fluorescence in water ($\lambda_{em}$=313 nm) to the six 1,2-dialkoxybenzenes that form its cage in the two CTV units. This led to the study of xenon binding equilibrium by heavy-atom quenching:

(1)

Xenon was previously shown to quench 2-phenanthrene sulfonate and pyrene bound to apomyoglobin, but this required a large overpressure of xenon due to its low affinity for the protein. In the current example, fluorescence quenching by xenon provided a sensitive method of measuring Xe binding, even at sub-stoichiometric Xe concentrations.

Fluorescence quenching experiments were conducted at 293 K with 1.5×10$^{-5}$ M solutions of TTPC in 1 mM, pH 7.2 phosphate buffer. A saturated xenon solution at 310 K ([Xe]= 3.3 mM) was titrated into the septum-sealed cuvette by gas-tight syringe. To obtain a saturated xenon measurement, xenon gas was bubbled directly into the cuvette. In all cases, fluorescence spectra were collected after thermal equilibration at 293 K (FIG. 2)

The fluorescence maxima were fitted to a single-site binding model using the following relationship.

$$\frac{[Xe@I]}{[Xe@I]+[I]} = \frac{[Xe]}{[Xe]+K_D}$$ (2)

where $K_D$ is the Xe dissociation constant for cryptophane TTPC. At xenon saturation, [Xe]=5.05 mM at 293 K and 1 atm, the cryptophane fluorescence was half quenched ($F_o/F$=2). No cryptophane impurities or concentration dependent phenomena were observed that might also contribute to partial fluorescence quenching. An association constant of 17,000±1800 M$^{-1}$ (1 std. dev.) was obtained at 293 K. This value is roughly twice the best $K_A$ values for cryptophane-A derivatives in water at rt that have been previously reported.

Xenon binding was also determined by isothermal titration calorimetry (ITC), which directly measured the heat released during Xe association. ITC measurements were undertaken in 20 mM, pH 7.5 phosphate buffer at 293 K and 310 K as well as in human plasma at 310 K (FIG. 3).

The association constants obtained from fits of ITC data at 293 K ($K_A$=1.73×10$^4$ M$^{-1}$, Table 5) and fluorescence quenching were in excellent agreement. A higher binding affinity ($K_A$=3.01×10$^4$ M$^{-1}$) was observed in buffer at physiological temperature, based on ΔS equal to 9.0 cal/mol K. It is apparent from the relative magnitudes of ΔH and −TΔS at 293 and 310 K in phosphate buffer that entropy was a major contributor to xenon binding. This was likely a consequence of the 20 water molecules that make up the first solvation sphere of the Xe atom in aqueous solution.

TABLE 5

Thermodynamic binding parameters of Xe @ I obtained by ITC

| | $K_A$ (M$^{-1}$ × 10$^4$) | ΔG (kcal mol$^{-1}$) | ΔH (kcal mol$^{-1}$) | TΔS (kcal mol$^{-1}$) |
|---|---|---|---|---|
| Buffer 293 K | 1.73 ± 0.17 | −5.69 | −3.14 ± 0.20 | 2.55 |
| Buffer 310 K | 3.01 ± 0.26 | −6.36 | −3.56 ± 0.13 | 2.80 |
| Plasma 310 K | 2.19 ± 0.22 | −6.16 | −6.04 ± 0.33 | 0.12 |

Xenon binding in plasma, while comparable to buffer at 310 K, showed significant differences in measured enthalpy and entropy. From Table 5 and the known thermodynamics of xenon partitioning into water, an upper limit of ΔH=−7.5 kcal/mol was calculated for the enthalpy of xenon binding to I. Thus, the measured ΔH of −6.04 kcal/mol, although larger than in buffer, appeared reasonable. Furthermore, the average literature value for xenon solubility in plasma at 310 K is 3.6 mM, which is ~10% higher than in buffer. These results suggest that xenon interacts with proteins and lipids in plasma, which reduces the contribution of entropy (TΔS=0.12, Table 1) relative to Xe binding I in buffer.

Example 8

Structure of a $^{129}$Xe-Cryptophane Biosensor Complexed with Human Carbonic Anhydrase II The α-carbonic anhydrases (CAs) are zinc metalloenzymes that catalyze the reversible hydration of CO$_2$ in forming HCO$_3^-$. The active site of an α-CA contains a catalytically essential Zn$^{2+}$ coordinated by three histidine residues at the bottom of a 15 Å deep cleft, and the tightest binding CA inhibitors developed to date contain a sulfonamide moiety that coordinates to Zn$^{2+}$ as a sulfonamidate anion. Notably, human isozyme II (CAII) is an ideal model system for exploring new inhibitor designs, some of which can be exploited in biosensing applications. In the present Example, CAII is utilized for the structure-based design of a xenon ($^{129}$Xe) biosensor for potential use as a magnetic resonance imaging (MRI) contrast agent.

The $^{129}$Xe isotope has a spin-½ nucleus, a >200 ppm chemical shift window in water, and a natural isotopic abundance of 26% (commercially available up to 86%), which makes it an appealing biomolecular probe for MRI. Moreover, $^{129}$Xe can be laser polarized to enhance MRI signals ~10,000-fold. Although current in vivo MRI applications are limited to functional lung imaging through the diffusion of Xe gas, the encapsulation of $^{129}$Xe within a cryptophane cage ($K_D \approx 30$ μM at 37° C. in phosphate-buffered solution) facilitates its use as a biosensor that can be targeted to specific proteins using an appropriate affinity tag. For example, racemic mixture of TTPC (FIG. 1a) has been designed to bind to the CA isozymes ($K_D$=60±20 nM against CAII in solution) and yields a distinctive $^{129}$Xe-MRI spectrum when bound to CAII. Reported herein, is the X-ray crystal structure of the CAII-TTPC-Xe complex at 1.70 Å resolution.

For structure determination, CAII was overexpressed in *Escherichia coli* and purified then incubated with a 2-fold excess of TTPC, concentrated to 10 mg/mL, and crystallized by the hanging drop vapor diffusion method. Crystals were cryoprotected in 15% glycerol and subsequently pressurized under 20 atm Xe for 30 min prior to flash cooling and X-ray data collection. The structure was refined to final $R_{work}$ and $R_{free}$ values of 0.23 and 0.25, respectively. TTPC coordinates to the active site $Zn^{2+}$ ion as the sulfonamidate anion, displacing the zinc-bound hydroxide ion of the native enzyme as previously observed in other complexes of CAII with benzenesulfonamide derivatives. The crystallographic occupancies of the biosensor and $Zn^{2+}$ are refined at 0.5.

Figure 10:
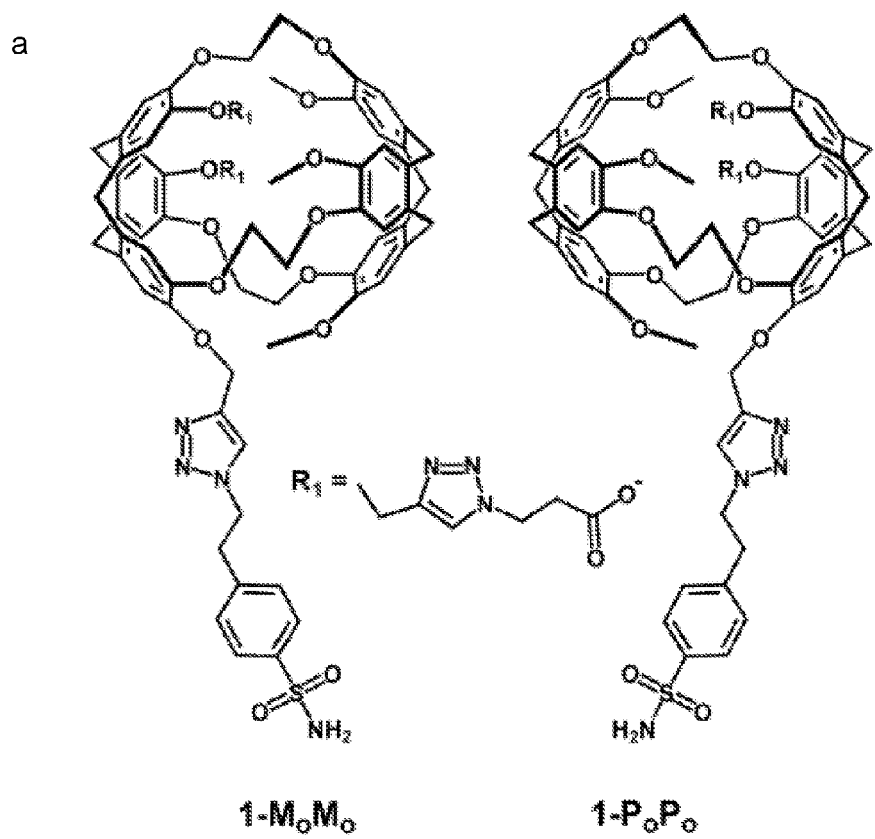
FIG. 10 shows (a) The $M_o/M_o$, and $P_o/P_o$, enantiomers of the cryptophane-A-derived CA biosensor. The benzenesulfonamide moiety serves as an affinity tag that targets the $Zn^{2+}$ ion, and the $R_1$ substituents contain triazole propionate moieties that enhance aqueous solubility. (b) Stereoview of a simulated annealing omit map showing both enantiomers of benzenesulfonamide-substituted di-triazole propionate cryptophane (DTPC)-$M_o/M_o$ (blue) and $P_o/P_o$, (red) bound in the active site (1.9 σ contour, teal). A Bijvoet difference Fourier map (2.0 σ, black) confirms the encapsulation of Xe (yellow). Coordination interactions with $Zn^{2+}$ (gray sphere) are indicated by dotted lines.
Figure 10:
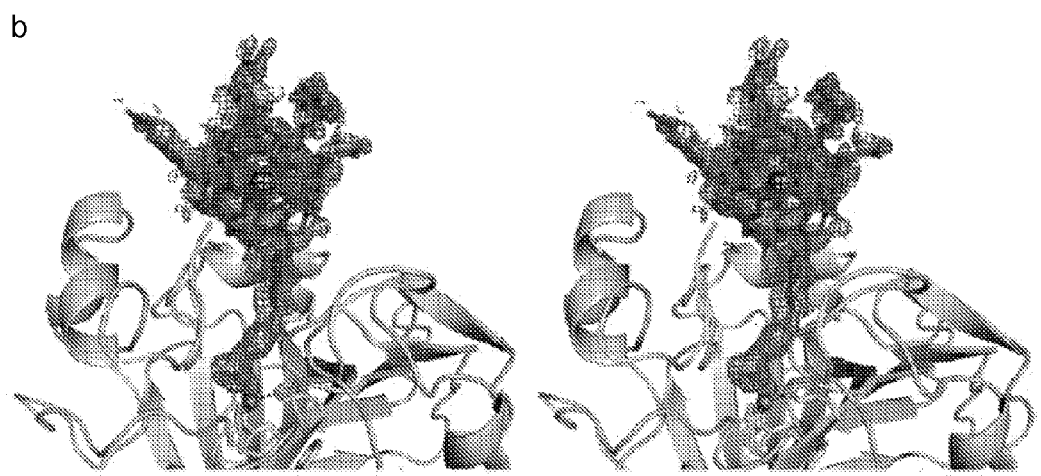
Figure 20:
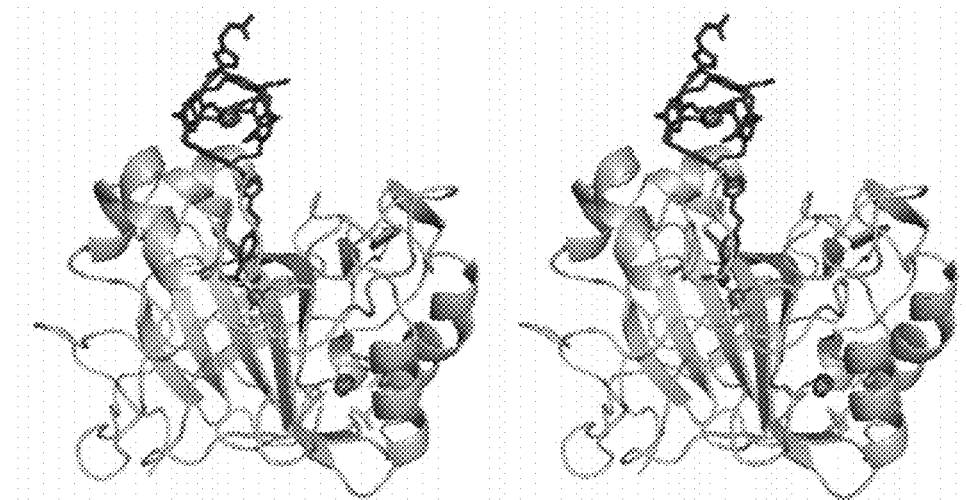
FIG. 20 shows a stereoview of an anomalous difference map (2.0 σ, black) that pinpoints the two Xe locations (yellow spheres). Only the $P_oP_o$ enantiomer of benzenesulfonamide ditriazole propionate cryptophane (red) is shown for clarity. Coordination interactions with $Zn^{2+}$ (grey sphere) are indicated with dotted lines.
Figure 21:
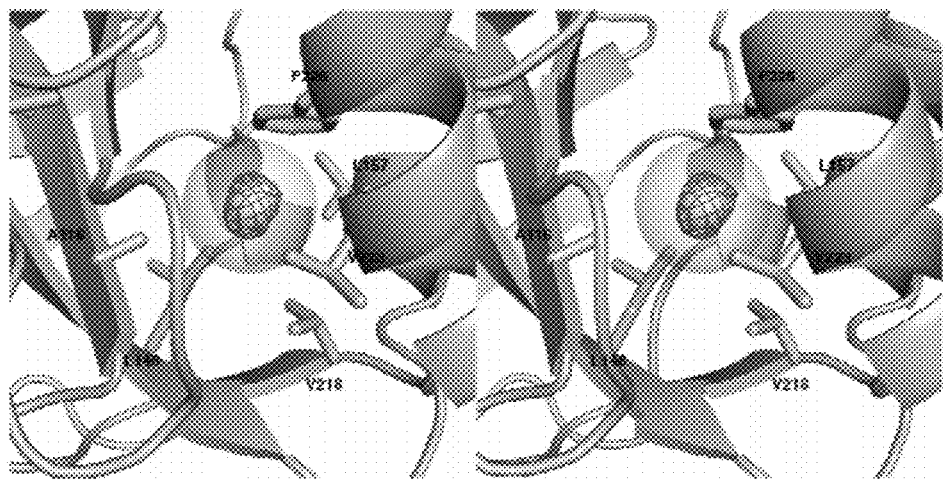
FIG. 21 shows a stereoview of an anomalous difference map (2.0 σ, black) that pinpoints the Xe (solid yellow sphere) location within the hydrophobic pocket defined by A116, L148, V218, V223, L157 and F226. The van der Waals surface of Xe (radius=2.16 Å) is shown as a translucent yellow sphere. The crystallographic occupancy of this Xe atom is 0.37.
Figure 22:
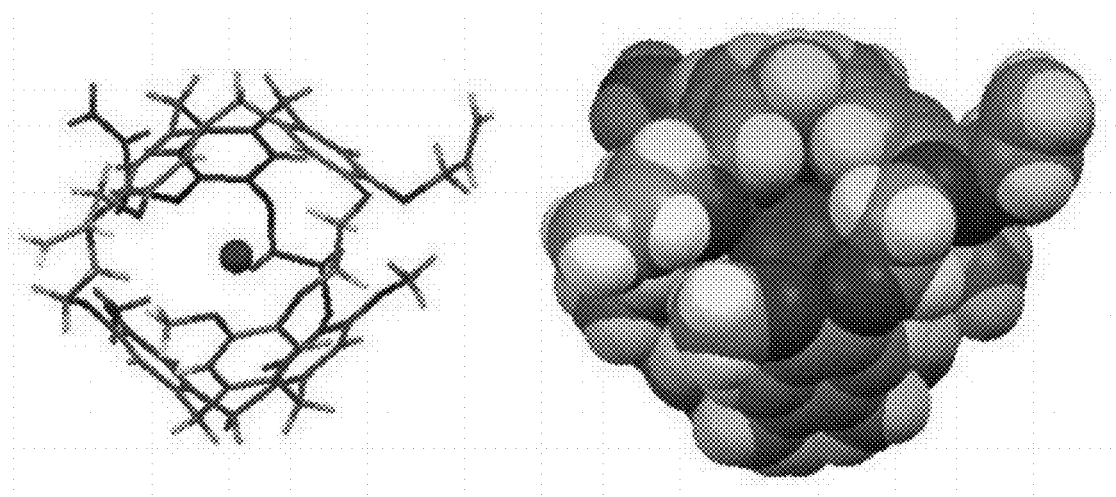
FIG. 22 shows X-ray crystal structure determination of tri-allyl cryptophane complexed with Xe.

The encapsulation of Xe within the cryptophane cage of TTPC is confirmed by inspection of the Bijvoet difference Fourier map calculated from anomalous scattering data (FIGS. 10b and 20). X-ray diffraction data were collected at a wavelength λ=0.9795 Å, which is far from the Xe $L_I$ edge of 2.27 Å. Nevertheless, the anomalous scattering component f" is 3.4 e⁻ for Xe, so the anomalous signal is still prominent at the wavelength of data collection. A second Xe binding site is observed in a hydrophobic pocket defined by A116, L148, V218, L157, V223, and F226 (FIG. 21). The crystallographic occupancies of these Xe sites refine to 0.50 and 0.37, respectively. Anomalous scattering peaks are absent from crystals not subject to Xe pressurization.

Notably, TTPC contains a chiral axis, and the electron density map reveals the binding of equal populations of both enantiomers (each refined with an occupancy of 0.25; FIG. 1). Overall, the binding of TTPC does not cause any significant structural changes in the active site, and the root-mean-square deviation is 0.34 Å for 256 C α atoms between the current structure and the unliganded enzyme (PDB 2CBA).

Figure 11:
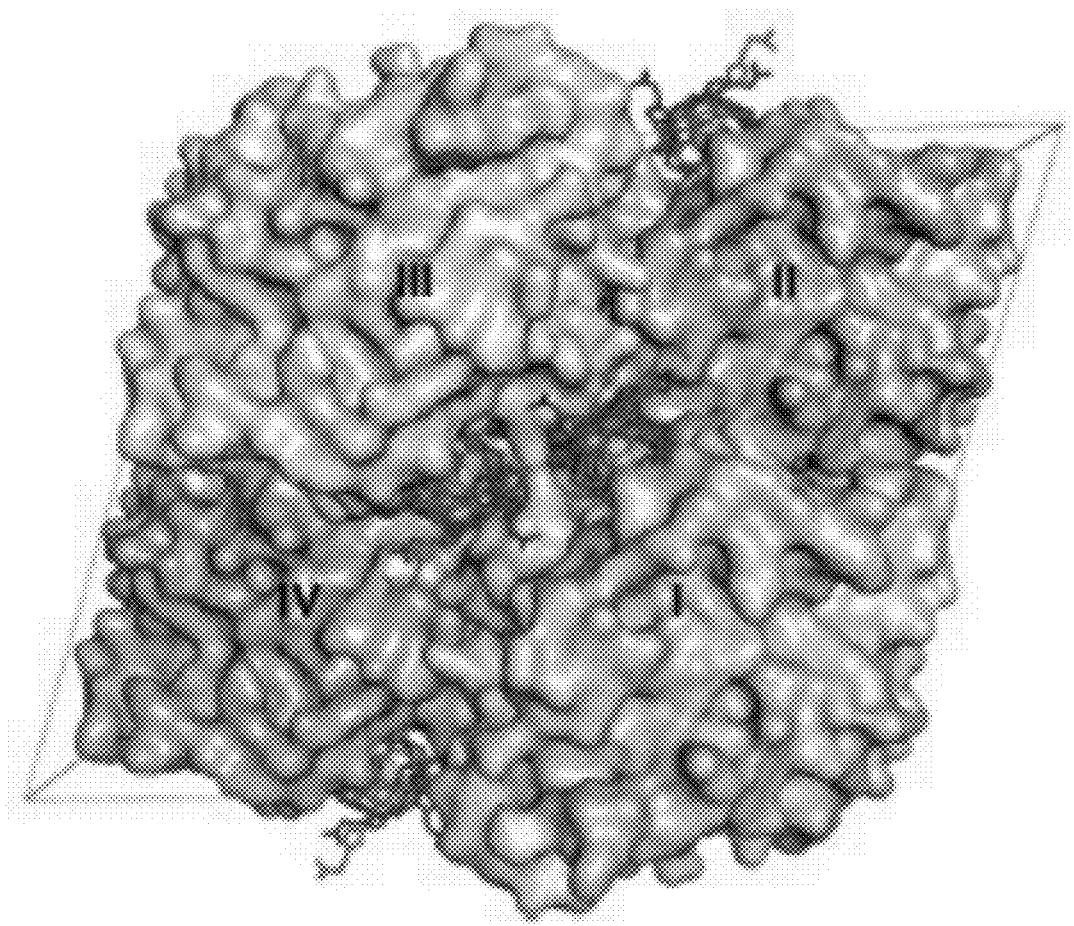
FIG. 11 shows the unit cell of CAII crystals in space group C2 contains four molecules: I (x, y, z), II (x+½, y+½, z), III (−x, y, −z), and IV (−x+½, y+½, −z). The binding of the benzenesulfonamide di-triazole propionate cryptophane (DTPC) in the active-site cleft of molecule I buries ~500 Å$^2$ of surface area. Crystal contacts bury an additional 540 Å$^2$ of the surface of triazole propionate cryptophane as follows: 270 Å$^2$ with molecule III, and 240 and 30 Å$^2$ with the front and back faces of molecule II, respectively. Molecule IV does not contact triazole propionate cryptophane bound to molecule I.
Figure 12:
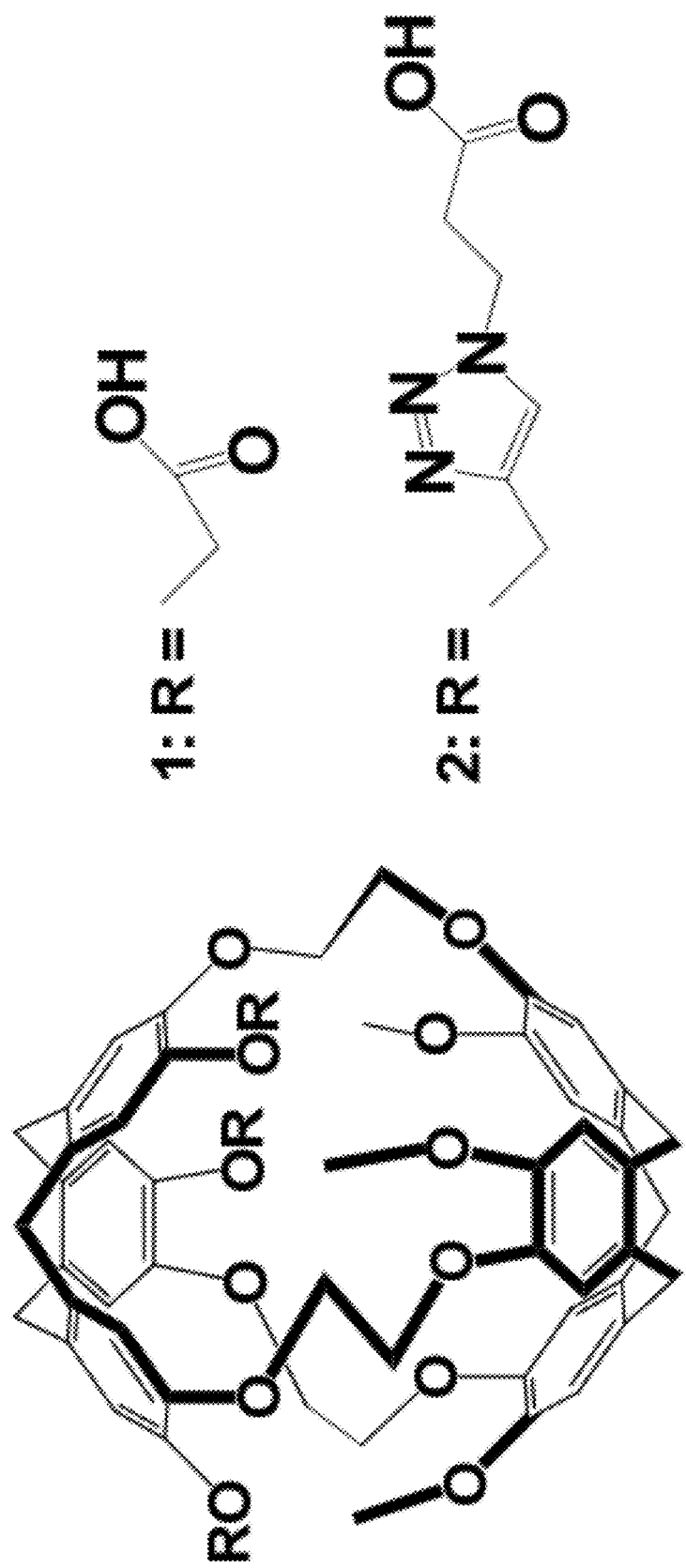
FIG. 12 shows triacetic acid-functionalized cyptophane (TAAC, 1) and tri-triazole propionate-functionalized cryptophane (TTPC, 2)

The total surface area of TTPC is ~1500 Å², of which ~500 Å² becomes solvent inaccessible due to contacts of TTPC within the active site cleft of CAII designated molecule I in FIG. 11. The surrounding CAII molecules in the unit cell (molecules II-IV) sequester an additional ~540 Å² of the surface area of 1 from solvent. Some structural changes are observed near the outer rim of the active site cleft where the cryptophane binds. The most notable change is observed for Q136, which rotates ~180° to make van der Waals contacts with the cryptophane and the symmetry-related cryptophane bound to molecule III in the crystal lattice. Other residues at the active site rim of molecule I that make close contacts with the cryptophane are G132 and P202. Additional structural changes in the crystal lattice result from the binding of TTPC to molecule I: in molecule II, H36 rotates ~90° to make a van der Waals contact with the cage, and Q137 of molecule III rotates ~90° to donate a hydrogen bond to an ether oxygen atom of TTPC.

Crystals belonged to space group C2 (unit cell parameters a=67.4 Å, b=50.0 Å, c=81.0 Å, β=107.1°) and were isomorphous with those of T199P CAII complexed with thiocyanate (PDB 1LG6). Two xenon sites were identified by inspection of the Bijvoet difference Fourier map calculated from anomalous data. The first site is near the opening of the active site cleft, 18 Å from $Zn^{2+}$ and 8 Å from the protein chain, and corresponds to the Xe atom encapsulated by the cryptophane (FIG. 20). The second Xe site is a hydrophobic pocket defined by A116, L148, V218, L157, V223 and F226, which is consistent with the known binding interactions of Xe in other systems (FIG. 21). Neither of those Xe sites are occupied in a crystal not pressurized in the xenon chamber.

Because the crystallographic occupancy was thus 0.5 for Xe encapsulated within the cryptophane moiety, and the electron density map indicated the binding of both cryptophane enantiomers, each enantiomer was refined with an occupancy of 0.25 (average B-factor=43 Å²). A total of 185 water molecules were included in later cycles of refinement. Data reduction and refinement statistics are recorded in Table 6.

TABLE 6

Data Collection and Refinement Statistics

| | CAII-1-Xe complex |
|---|---|
| Data Collection | |
| Resolution, Å | 38.7-1.70 |
| Total reflections measured[a] | 52826 (4698) |
| Unique reflections measured[a] | 27728 (2556) |
| $R_{merge}$[a,b] | 0.078 (0.496) |
| I/σ(I)[a] | 27.1 (2.3) |
| Completeness (%)[a] | 97.0 (90.3) |
| Multiplicity[a] | 3.9 (3.7) |
| Refinement | |
| Reflections used in refinement/test set | 24730/1139 |
| $R_{work}$ | 0.226 |
| $R_{free}$ | 0.249 |
| Protein atoms[c] | 2049 |
| Water molecules[c] | 185 |
| Xe atoms[c] | 2 |
| Cryptophane-A-benzenesulfonamide atoms[c] | 103 |
| R.m.s deviations | |
| Bond lengths, Å | 0.016 |
| Bond angles, ° | 1.8 |
| Dihedral angles, ° | 22.4 |
| Improper dihedral angles, ° | 0.7 |
| Average B-factors, Å² | |
| Main chain | 31 |
| Side chain | 35 |
| Xe atoms | 43 |
| Zn atom | 28 |
| Cryptophane-A-benzenesulfonamide atoms | 42 |
| Solvent | 40 |
| Ramachandran Plot[d] | |
| Allowed (%) | 86.6 |
| Additionally allowed (%) | 12.5 |
| Generously allowed (%) | 0.9 |
| Disallowed (%) | 0.0 |

[a]Number in parentheses refer to the outer 0.1 Å shell of data.
[b]$R_{merge} = \Sigma|I - \langle I \rangle|/\Sigma I$, where I is the observed intensity and $\langle I \rangle$ is the average intensity calculated for replicate data.
[c]Per asymmetric unit
[d]Ramachandran plot statistics calculated for non-proline and non-glycine residues using PROCHECK.

Although the pendant propionates appear to be more disordered than the cryptophane and are characterized by correspondingly weaker electron density, a hydrogen bond between a propionate moiety and Q53 of molecule II is observed. The relative dearth of strong cryptophane-protein interactions may explain why the affinity of TTPC measured by ITC is only slightly better than that measured for the parent triazole benzenesulfonamide lacking the cryptophane ($K_D$=100±10 nM).

Limited hydrogen bond interactions between CAII and the cryptophane moiety of TTPC may be advantageous for the use of cryptophanes as $^{129}$Xe biosensors. Translational and rotational freedom, the consequence of a flexible linker between the cryptophane and the benzensulfonamide, allows the cage to reorient rapidly in situ, independently of the protein, to result in decreased correlation times and narrower line widths that increase the sensitivity of $^{129}$Xe NMR measurements in solution.

Example 9

Multiple Targeting

A small family of tri-functionalized cryptophanes is developed, each of which gives a distinct Xe-129 NMR chemical shift, and is subsequently functionalized and targeted to a different biomarker. The tri-functionalized cryptophanes are synthesized having different heteroatoms, such as sulfur, nitrogen and the like, as well as different pendant moieties that improve solubility or targeting, and serve to modulate the Xe-129 NMR chemical shift.

Making small changes in the size, composition and polarity of the cryptophane cage has a big effect on Xe-129 NMR chemical shift.

Example 10

Synthesis of a Tri-Functionalized Cryptophane without Alcohol Protection or Deprotection Steps Large quantities of tri-substituted cryptophane to be used for further synthesis of water-soluble modified cryptophanes at milligram-to-gram scales are needed. A shorter, 6-step synthesis of tripropargyl cryptophane (6, FIG. 23) from commercial starting materials (vanillyl alcohol, 1,2-dibromoethane, and 3,4-dihydroxybenzaldehyde) was developed that avoids the requirement for vanillyl alcohol protection and deprotection steps. The key step is a step that eliminates the need for allyl group protection/deprotection to obtain a functionalized cyclotriveratrylene (CTV) intermediate by a widely used method. In one example, the step involves the trimerization of compound 1 (FIG. 23) to yield tri-(2-bromoethyl)cyclotriveratrylene 2 (FIG. 23), This intermediate is then reacted with three equivalents of benzaldehyde 3 (FIG. 23). Borohydride reduction and cyclization with scandium triflate then gives tri-propargyl cryptophane 6 (FIG. 23) in just 6 steps. Overall yield for this synthetic route is 5.3%, and is 3 fewer steps and at least 50% higher yielding than the previously published 9-step procedure. See Hill, P. A., Wei, Q., Eckenhoff, R. G., Dmochowski, I. J. Thermodynamics of xenon binding to cryptophane in water and human plasma. *J. Am. Chem. Soc.* 129, 9262-9263 (2007).

Synthetic Procedures and Analytical Data (4-(2-bromoethoxy)-3-methoxyphenyl)methanol (1, FIG. 23)) and 4-hydroxy-3-(prop-2-ynyloxy)benzaldehyde (3, FIG. 23)) was prepared according to the procedure published in Wei, Q., Seward, G. K., Hill, P. A., Patton, B., Dimitrov, I. E., Kuzma, N. N., Dmochowski, I. J. Designing Xe-129 NMR biosensors for matrix metalloproteinase detection. *J. Am. Chem. Soc.* 128, 13274-13283 (2006).

2,7,12-Tris-(2-bromoethoxy)-3,8,13-trimethoxy-10,15-dihydro-2H-tribenzo[a,d,g]cyclononene (2, FIG. 23): Compound 1 of FIG. 23 (3.0 g, 11.50 mmol) and Sc(OTf)$_3$ (113.2 mg, 0.23 mmol) were dissolved in 25 mL CH$_2$Cl$_2$. The reaction was purged with nitrogen for 5 min and then refluxed overnight with stirring and filtered following standard workup procedure. The crude material was purified by silica gel flash column chromatography (CH$_2$Cl$_2$→2:98 Et$_2$O:CH$_2$Cl$_2$) to yield 1.21 g (1.66 mmol, 43% yield) of 2 as a white powder. TLC (silica gel, 5% Et$_2$O/CH$_2$Cl$_2$): R$_{f(2)}$=0.75. mp: 81-82° C. $^1$H NMR (CDCl$_3$) δ(ppm): 6.93 (3H, s, CH$_{Ar}$), 6.85 (3H, s, CH$_{Ar}$), 4.74 (3H, d, J=13.7 Hz, H$_{ax}$), 4.30 (6H, t, J=6.5 Hz, —O—CH$_2$—CH$_2$—Br), 3.83 (9H, s, —O—CH$_3$), 3.58 (6H, t, J=6.7 Hz, —O—CH$_2$—CH$_2$—Br), 3.55 (3H, d, J=13.8 Hz, H$_{eq}$). $^{13}$C NMR (CDCl$_3$) δ (ppm): 149.2 (3C$_{Ar}$), 146.1 (3C$_{Ar}$), 134.0 (3C$_{Ar}$), 131.0 (3C$_{Ar}$), 118.0 (3C$_{Ar}$), 114.1 (3C$_{Ar}$), 70.1 (3C, O—CH$_2$—CH$_2$—Br), 56.4 (3C, —OCH$_3$), 36.6 (3C, Ar—CH$_2$—Ar), 29.4 (3C, O—CH$_2$—CH$_2$—Br). HRMS calculated for C$_{30}$H$_{33}$Br$_3$O$_6$(M+Na$^+$) 748.9725. found 748.9739.

2,7,12-Tris-[2-[4-formyl-2-propargyloxyphenoxy] ethoxy]-3,8,13-trimethoxy-10,15-dihydro-2H-tribenzo[a,d,g]cyclononene (4, FIG. 23): Compound 3 of FIG. 23 (558.5 mg, 3.17 mmol) and Cs$_2$CO$_3$ (1.0 g, 3.17 mmol) were added to an oven-dried flask under nitrogen atmosphere. Anhydrous DMSO (30 mL) was added by syringe and the reaction mixture was stirred for 30 min Compound 2 (FIG. 23) (700.0 mg, 0.96 mmol) was then added and the reaction stirred at 55° C. overnight. The reaction mixture was filtered and the crude material was purified by column chromatography (CH$_2$Cl$_2$→5:95 Et$_2$O:CH$_2$Cl$_2$) to yield 585 mg (0.58 mmol, yield: 60%) of 4 (FIG. 23) as a white solid. TLC (silica gel, 10% Et$_2$O/CH$_2$Cl$_2$): R$_{f(4a)}$=0.16. mp: 103-104° C. $^1$H NMR (CDCl$_3$) δ(ppm): 9.87 (3H, s, (H)C=O), 7.55 (3H, s, CH$_{Ar}$), 7.50 (3H, d, J=8.2 Hz, CH$_{Ar}$), 7.05 (3H, d, J=8.2 Hz, CH$_{Ar}$), 7.01 (3H, s, CH$_{Ar}$), 6.86 (3H, s, CH$_{Ar}$), 4.74-4.77 (9H, m, H$_{ax}$, —OCH$_2$C≡CH), 4.40-4.44 (12H, m, O—CH$_2$—CH$_2$—O), 3.75 (9H, s, —O—CH$_3$), 3.57 (3H, d, J=13.8 Hz, H$_{eq}$), 2.52 (3H, t, J=2.3 Hz, —OCH$_2$C≡CH). $^{13}$C NMR (CDCl$_3$) δ(ppm): 190.8 (3C, C=O), 154.5 (3C$_{Ar}$), 149.0 (3C$_{Ar}$), 147.8 (3C$_{Ar}$), 147.0 (3C$_{Ar}$), 133.6 (3C$_{Ar}$), 132.2 (3C$_{Ar}$), 131.0 (3C$_{Ar}$), 127.2 (3C$_{Ar}$), 117.4 (3C$_{Ar}$), 114.3 (3C$_{Ar}$), 113.8 (3C$_{Ar}$), 113.0 (3C$_{Ar}$), 78.2 (3C, C≡CH), 76.6 (3C, C≡CH), 68.4 (3C, —O—CH$_2$—CH$_2$—O—), 68.0 (3C, —O—CH$_2$—CH$_2$—O—), 57.1 (3C, —OCH$_2$C≡CH), 56.5 (3C, —OCH$_3$), 36.7 (3C, Ar—CH$_2$—Ar). HRMS calculated for C$_{60}$H$_{54}$O$_{15}$ (M+Na$^+$) 1037.3360. found 1037.3384.

2,7,12-Tris-[2-[4-(hydroxymethyl)-2-propargyloxyphenoxy]ethoxy]-3,8,13-trimethoxy-10,15-dihydro-2H-tribenzo[a,d,g]cyclononene (5, FIG. 23): Compound 4 (FIG. 23) (500.0 mg, 0.49 mmol) was dissolved in 5 mL THF and 20 mL MeOH. The solution was cooled to −10° C. in a salted ice bath, followed by the addition of sodium borohydride (185.3 mg, 4.90 mmol, 10 eq.). The reaction mixture was stirred at 0° C. for 20 min, then allowed to warm to rt and stirred overnight. The reaction was evaporated under reduced pressure and to the solids was added water (25 mL). HCl (25 mL, 1 M) was added slowly, followed by extraction with ethyl acetate (3×25 mL). The combined organics were washed once with 1 M HCl (25 mL), once with water (25 mL), and once with brine (25 mL). After filtration the solvent was removed under reduced pressure. The crude material was purified by column chromatography (5:95 MeOH:CH$_2$Cl$_2$) to yield 438.0 mg (0.42 mmol, 87% yield) of 5 (FIG. 23) as a white solid. TLC (silica gel, 5% MeOH/CH$_2$Cl$_2$): R$_{f(5a)}$=0.25. $^1$H NMR (CDCl$_3$) δ(ppm): 7.03 (3H, s, CH$_{Ar}$), 6.98 (3H, s, CH$_{Ar}$), 6.89 (6H, m, CH$_{Ar}$), 6.81 (3H, m, CH$_{Ar}$), 4.73 (3H, d, J=13.6, H$_{ax}$), 4.59 (12H, m, Ar—CH$_2$—OH, —OCH$_2$C≡CH), 4.34 (12H, m, —O—CH$_2$—CH$_2$—O—), 3.70 (9H, s, —O—CH$_3$), 3.53 (3H, d, J=13.8 Hz, H$_{eq}$), 2.44 (3H, t, J=2.2 Hz, —OCH$_2$C≡CH). $^{13}$C NMR (CDCl$_3$/DMSO-d6) δ(ppm): 148.5 (3C$_{Ar}$), 148.3 (3C$_{Ar}$), 147.4 (3C$_{Ar}$), 146.8 (3C$_{Ar}$), 134.8 (3C$_{Ar}$), 133.2 (3C$_{Ar}$), 132.1 (3C$_{Ar}$), 121.1 (3C$_{Ar}$), 116.8

(3C$_{Ar}$), 114.9 (3C$_{Ar}$), 114.6 (3C$_{Ar}$), 114.0 (3C$_{Ar}$), 78.8 (3C, —C≡CH), 75.7 (3C, —C≡CH), 68.3 (3C, Ar—CH$_2$—OH), 67.9 (3C, —O—CH$_2$—CH$_2$—O—), 64.2 (3C, —O—CH$_2$—CH$_2$—O—), 57.1 (3C, —OCH$_2$C≡CH), 56.2 (3C, —OCH$_3$), 36.3 (3C, Ar—CH$_2$—Ar). HRMS calculated for C$_{60}$H$_{60}$O$_{15}$ (M+Na$^+$) 1043.3830. found 1043.3751.

Tripropargyl Cryptophane-A: Dichloromethane (30 mL) was added to the flask which was charged with compound 5 (FIG. 23) (100.0 mg, 0.10 mmol) and Sc(OTf)$_3$ (5.0 mg, 0.01 mmol). The reaction was purged with nitrogen for 5 min and then refluxed overnight with stirring. The reaction mixture was filtered following standard workup procedure. The crude material was purified by silica gel flash column chromatography (CH$_2$Cl$_2$→5:95 Acetone:CH$_2$Cl$_2$) to yield 62 mg (0.06 mmol, 65% yield) of 6 (FIG. 23) as a white powder. TLC (silica gel, 10% Acetone/CH$_2$Cl$_2$): R$_{f(6a)}$=0.73. $^1$H NMR (CDCl$_3$) δ(ppm): 6.90 (3H, s, CH$_{Ar}$), 6.79 (3H, s, CH$_{Ar}$), 6.76 (3H, s, CH$_{Ar}$), 6.69 (3H, s, CH$_{Ar}$), 4.55-4.71 (12H, m, —OCH$_2$C≡CH, H$_{ax}$), 4.16 (m, 12H, —OCH$_2$CH$_2$O—), 3.82 (s, 9H, —OCH$_3$), 3.42 (3H, d, J=13.8 Hz, H$_{eq}$), 3.41 (3H, d, J=13.9 Hz, H$_{eq}$), 2.69 (3H, t, J=2.3 Hz, —OCH$_2$CCH). $^{13}$C NMR (CDCl$_3$) δ(ppm): 149.9 (3C$_{Ar}$), 148.1 (3C$_{Ar}$), 147.7 (3C$_{Ar}$), 146.8 (3C$_{Ar}$), 134.3 (6C$_{Ar}$), 133.6 (3C$_{Ar}$), 131.7 (3C$_{Ar}$), 122.1 (3C$_{Ar}$), 120.9 (3C$_{Ar}$), 117.6 (3C$_{Ar}$), 114.2 (3C$_{Ar}$), 79.2 (3C, —C≡CH), 76.4 (3C, —C≡CH), 69.7 (3C, —O—CH$_2$—CH$_2$—O—), 69.6 (3C, —O—CH$_2$—CH$_2$—O—), 57.6 (3C, —OCH$_2$C≡CH), 56.4 (3C, —OCH$_3$), 36.45 (6C, Ar—CH$_2$—Ar). HRMS calculated for C$_{60}$H$_{54}$O$_{12}$ (M+Na$^+$) 989.3553. found 989.3513.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A biosensor comprising a hyperpolarized noble element complexed with a tri-functionalized cryptophane, wherein the tri-functionalized cryptophane comprises first and second cyclotriveratrylene (CTV) units having a dipole moment therebetween.

2. The biosensor of claim 1, wherein at least one affinity tag is coupled to the tri-functionalized cryptophane.

3. The biosensor of claim 1, wherein said noble element is an isotope of xenon.

4. The biosensor of claim 3, wherein the hyperpolarized noble element is $^{129}$Xe or $^{133}$Xe.

5. The biosensor of claim 2, wherein the affinity tag is a folate, a glucose moiety or other carbohydrate, a peptoid, a small molecule, or an RGD peptide.

6. The biosensor of claim 2, wherein there are two or three affinity tags coupled to the tri-functionalized cryptophane.

7. The biosensor of claim 6, wherein the two or three affinity tags coupled to the tri-functionalized cryptophane are the same.

8. The biosensor of claim 6, wherein the two or three affinity tags coupled to the tri-functionalized cryptophane are different.

9. The biosensor of claim 1, wherein the tri-functionalized cryptophane is functionalized with a triazole propionate moiety, triacetic acid moiety, long-chain PEG, amines, amides, sulfones, esters, peptides, sugars, polymers, or combinations thereof.

* * * * *